United States Patent [19]

Farrelly

[11] Patent Number: 5,630,664
[45] Date of Patent: May 20, 1997

[54] HAND HELD APPARATUS FOR PERFORMING MEDICAL CALCULATIONS

[76] Inventor: Patricia A. Farrelly, 431 Mills Dr., Benicia, Calif. 94510

[21] Appl. No.: 575,742

[22] Filed: Dec. 20, 1995

[51] Int. Cl.⁶ .................................................. G06F 19/00
[52] U.S. Cl. ...................... 128/695 R; 128/696
[58] Field of Search .................... 128/695, 696, 128/710; 364/413.01, 413.02, 413.03, 413.05, 413.06

[56] References Cited

U.S. PATENT DOCUMENTS

| | | |
|---|---|---|
| 3,737,863 | 6/1973 | Rowland et al. . |
| 3,921,147 | 11/1975 | Fuhr et al. . |
| 3,940,742 | 2/1976 | Hudspeth et al. . |
| 4,290,113 | 9/1981 | Haker et al. . |
| 4,591,974 | 5/1986 | Dombush et al. . |
| 4,709,331 | 11/1987 | Barkett et al. ............... 364/413.01 |
| 4,736,322 | 4/1988 | Clifford . |
| 4,779,199 | 10/1988 | Yoneda et al. . |
| 4,803,625 | 2/1989 | Fu et al. . |
| 4,807,170 | 2/1989 | Kulli et al. ............... 364/413.01 |
| 4,835,372 | 5/1989 | Gombrich et al. . |
| 4,916,441 | 4/1990 | Gombrich . |
| 4,945,477 | 7/1990 | Edwards . |
| 4,975,842 | 12/1990 | Darrow et al. . |
| 4,991,091 | 2/1991 | Allen . |
| 5,050,612 | 9/1991 | Matsumura . |
| 5,056,059 | 10/1991 | Tivig et al. . |
| 5,111,396 | 5/1992 | Mills et al. . |
| 5,140,519 | 8/1992 | Friesdorf et al. . |
| 5,183,051 | 2/1993 | Kraidin et al. . |
| 5,243,696 | 9/1993 | Carr et al. . |
| 5,276,612 | 1/1994 | Selker . |
| 5,298,021 | 3/1994 | Sherer ............... 364/413.02 |
| 5,321,800 | 6/1994 | Lesser . |

FOREIGN PATENT DOCUMENTS 299667  1/1989  European Pat. Off. .

*Primary Examiner*—William E. Kamm
*Assistant Examiner*—Carl H. Layno
*Attorney, Agent, or Firm*—Daniel J. Hulseberg; Mayer, Brown & Platt

[57] ABSTRACT

Hand-held apparatus for performing medical calculations includes a compact housing capable of being held within a hand of an operator. Provided in the housing is a data entry pad for selecting one of the medical calculations and entering data required for execution of the selected medical calculation, and a scanner and converter to input ECG waveforms as machine readable image data. A controller including a memory having the medical calculations stored therein is provided in the housing in communication with the data entry pad and the converter. The controller is configured to retrieve the selected medical calculation from the memory, provide prompts for entry of the data required for execution of the selected medical calculation, and provide a request for validation of each data entry made using the data entry pad. Included in the memory are medical calculations for calculating relevant measurements of the inputted ECG waveforms, including the PR Interval, the QRS Complex, the QT Segment, the ST Segment and the ventricular rate. The controller is configured to identify the start point and the end point of the relevant measurement and determine the difference therebetween. A display also is provided in the housing in communication with the controller to display each prompt for required data and each request for validation provided by the controller, as well as the data entries made and the results obtained.

26 Claims, 19 Drawing Sheets

HAND HELD APPARATUS FOR PERFORMING MEDICAL CALCULATIONS

BACKGROUND OF THE INVENTION

1. Field of the Invention

The present invention relates to a hand-held apparatus for performing medical calculations. Particularly, the present invention is directed to a compact, self-contained apparatus capable of performing medical calculations accurately by prompting and validating data entries, as well as identifying relevant measurements from graphical information such as electrocardiogram waveforms.

2. Description of Related Art

Nurses and health care professionals are responsible for accurately providing a variety of calculations and measurements to assist in the treatment of patients. In addition to continuously monitoring and recording the body functions of a patient, such as pulse and blood pressure, these health care professionals must also calculate and convert prescriptions into the appropriate dosage of medication available to satisfy the size and age of the patient, as well as interpret laboratory results to determine Arterial Blood Gases (ABGs) and other conditions. These medical calculations typically are performed bedside, often in a stressful or difficult environment.

With regard to cardiac care patients, an additional duty of the health care professional is to inspect ECG/EKG waveforms that are printed from a bedside cardiac monitor. For example, the health care professional typically obtains a six-second rhythm strip from the bedside monitor and measures various intervals along the waveform printed on the rhythm strip that reflect the current cardiac status of the patient. If the measured value falls outside of a predetermined range, the health care professional must then contact the responsible physician to order more extensive testing using twelve-lead ECG diagnostic machines. Unlike the bedside cardiac monitors, these twelve-lead ECG diagnostic machines are more complex and expensive to operate.

To perform these responsibilities, the health care professional currently must rely on a variety of tools or equipment. Such equipment includes a clock, a stop watch, nomograms, charts, formulae, a calculator and a pair of calipers. Because the health care professional must constantly be on his or her feet, it is difficult to ensure that these tools will be readily accessible when needed. Additionally, the health care professional must often rely on memory rather than carrying charts and books of formulae.

In making these calculations and measurements, a simple mistake could prove to be life threatening. Accuracy is crucial. Therefore, it is important that the health care professional verify his or her calculations and measurements, and maintain thorough records. Due to the stressful environment associated with emergency situations, as well as the long and difficult hours typically required in the health care profession, there often is not an opportunity verify such calculations. Accuracy also is impaired when the health care professional must rely on his or her eyesight to read and interpret nomograms and ECG/EKG waveforms.

Several apparatus have been developed to assist health care professionals in performing and recording medical calculations. For example, U.S. Pat. No. 3,940,742 issued to Hudspeth et al. discloses a portable data acquisition device used for transferring various patient parameters to a printer. U.S. Pat. No. 4,591,974 to Dornbush et al. is directed to an information recording and retrieval system, which includes a number of hand held computers in communication with a host computer. Each hand held computer is used for entering medical data in a preprogrammed tabular format for subsequent transfer to and manipulation by the host microcomputer. The portable handheld terminal of the U.S. Pat. No. 4,916,441, issued to Gombrich, likewise is provided in communication via a local area network with a central file server for access to documented patient information, test results and physician orders, as well as for bedside data input using preprogrammed bar code entries.

With regard to graphical information, U.S. Pat. No. 5,111,396 to Mills et al. discloses a portable ECG data-storage apparatus for the capture, storage and playback of selective "windows" of successive plural-lead ECG data records. This is performed by connecting the apparatus to a conventional ECG machine, and then converting the captured analog signals into digital data for subsequent storage and playback. A risk management system is disclosed by U.S. Pat. No. 5,276,612 to Selker, which receives waveform signals from a conventional ECG machine and generates characteristic values for use by a predictive instrument.

Although these various devices are beneficial in the health care profession, each requires communication with a larger host computer or similar base equipment. The use of such a network of equipment is generally complex to operate and expensive to purchase and maintain. A few self-contained apparatus have been developed, such as the self-contained minicomputer for calculating and converting between known medical units disclosed by U.S. Pat. No. 4,290,113 to Haker et al. and the self-contained portable monitoring apparatus disclosed by U.S. Pat. No. 5,050,612 to Matsumura. However, these devices only offer a few limited functions. Additionally, there is no known manner of validating data entry for accuracy.

In view of the above, there remains a need for a self-contained, hand-held apparatus capable of accurately performing medical calculations. Particularly, there remains a need for a hand-held apparatus that allows simple selection and execution of a desired medical calculation, and validates proper entry of required data to ensure accuracy. There likewise remains a need for a hand-held apparatus that easily and accurately calculates relevant measurements from graphical information, such as electrocardiogram waveforms.

SUMMARY OF THE INVENTION

The purpose and advantages of the invention will be set forth in and apparent from the description and drawings that follow, as well as will be learned by practice of the invention. Additional advantages of the invention will be realized and attained by the elements of the apparatus and method particularly pointed out in the appended claims.

To achieve these and other advantages and in accordance with the purpose of the invention, as embodied and broadly described herein, a hand-held apparatus is provided for performing various medical calculations. The hand-held apparatus includes a compact housing capable of being held within a hand of an operator. A data entry pad is provided in the housing for selecting one of the medical calculations and entering data required for execution of the selected medical calculation. An input device, such as a scanner, also is provided in the housing to input graphical information. The graphical information is converted into corresponding machine readable image data, when necessary, by a converter.

The hand-held apparatus also includes a controller provided in the housing in communication with the data entry pad and the converter. The controller includes a memory having the various medical calculations stored therein. To execute the medical calculation selected using the data entry pad, the controller is configured to retrieve the selected medical calculation from the memory. The controller also is configured to provide prompts for entry of the data required for execution of the selected medical calculation. Once all required data is entered, the controller is configured to provide a request for validation of each data entry made using the data entry pad.

If graphical information is inputted using the scanner and converter, the controller is configured to calculate a relevant measurement of the graphical information. Particularly, the relevant measurement of the graphical information includes an interval having a start point and an end point. The controller therefore is configured to calculate the relevant measurement of the inputted graphical information by identifying the start point and the end point and determining the difference therebetween using the image data from the converter. This is accomplished by including at least one medical calculation stored within the memory of the controller for calculating the relevant measurement of the inputted graphical information. In the preferred embodiment, the relevant measurement includes at least one of a PR Interval, a QRS Complex, a QT Segment, an ST Segment and a ventricular rate obtained from the inputted electrocardiogram waveform. The apparatus also can determine whether the ventricular rate is regular or irregular if the inputted electrocardiogram waveform includes at least three R waves.

A display also is provided in the housing in communication with the controller. The display is configured to display each prompt for required data and each request for validation provided by the controller, as well as the data entry made using the data entry pad. The display likewise is configured to display the results obtained by execution of the selected medical calculation, including the relevant measurement of inputted graphical information calculated by the controller.

It is to be understood that both the foregoing general description and the following detailed description are exemplary and provided for purposes of explanation only, and are not restrictive of the invention, as claimed.

BRIEF DESCRIPTION OF THE DRAWINGS

The accompanying drawings, which are incorporated in and constitute a part of this specification, illustrate the preferred embodiment of the invention, and together with the description, serve to explain the principles of the invention.

DETAILED DESCRIPTION OF THE PREFERRED EMBODIMENT

Figure 1:
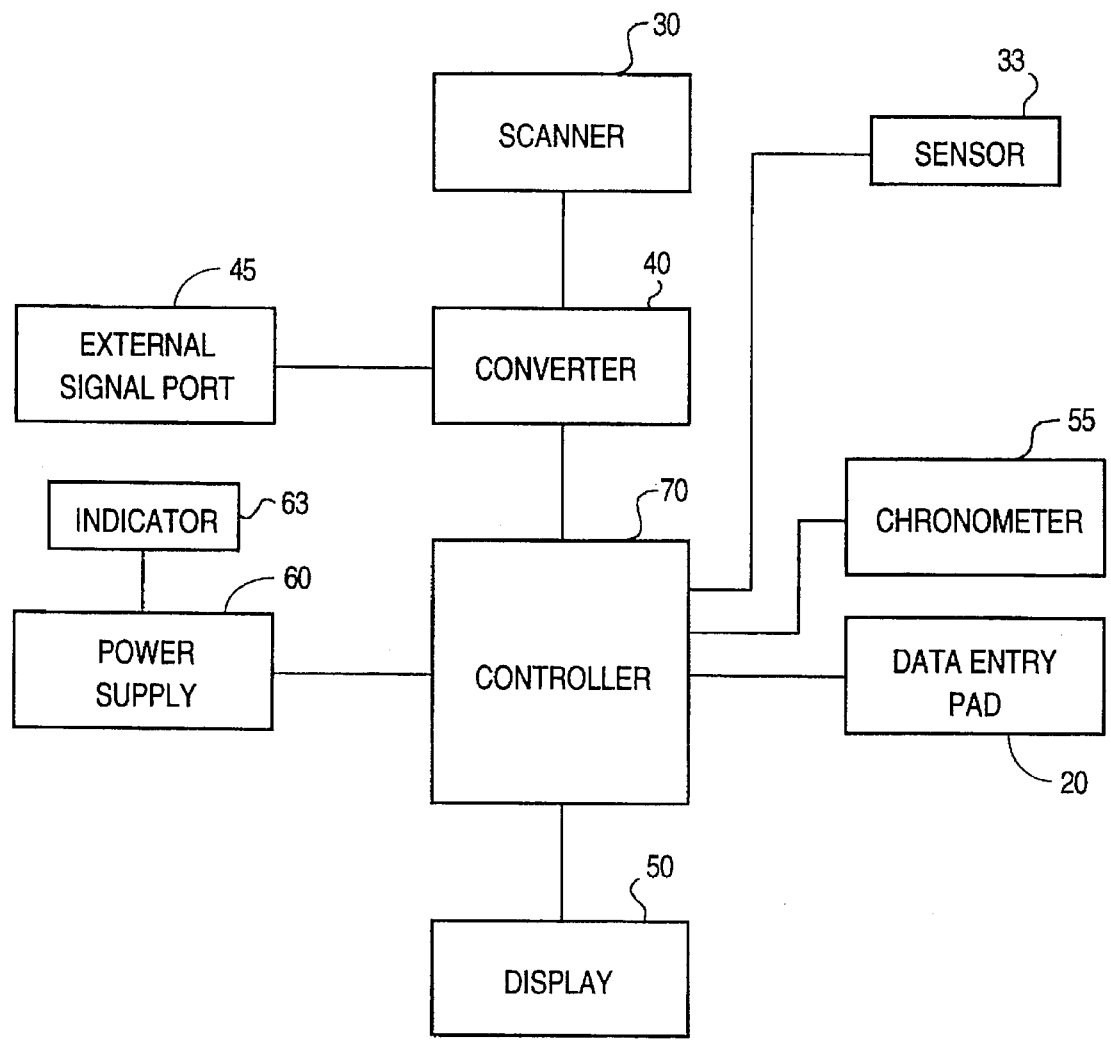
FIG. 1 is a block diagram showing components of the hand-held apparatus of the of the present invention.

Reference will now be made in detail to the present preferred embodiment of the hand-held apparatus of the invention, examples of which are illustrated in the accompanying drawings. Wherever possible, the same reference characters will be used throughout the drawings to refer to the same or like parts. The method of using the present invention will be described in conjunction with the detailed description of the hand-held apparatus.

In accordance with the present invention, a hand-held apparatus is provided for performing medical calculations. Particularly, the hand-held apparatus of the invention is a self-contained unit capable of storing and executing a variety of medical calculations, as well as validating data entries for accuracy and identifying data entries that are suspicious of inaccuracy. Such medical calculations stored and executed by the hand-held apparatus of the present invention not only relate to the determination of body conditions and prescribed doses of medicine, but also to the determination of relevant measurements from inputted graphical information.

For purpose of illustration and not limitation, FIG. 1 provides a block diagram showing various components of the hand-held apparatus of the present invention, which is designated generally by reference character 100. Particularly, a controller 70 is provided to execute selected medical calculations using entered data and to calculate relevant measurements from inputted graphical information. The controller 70 includes a memory having the various desired medical calculations stored therein. In communication with the controller 70 are a data entry pad 20, a scanner 30 with an associated analog-to-digital converter 40, and a display 50. A power supply 60 also is provided in communication with controller 70. All of these components are provided in a compact housing 10 of the hand-held apparatus 100 so as to provide a self-contained unit, as will be described in greater detail below.

FIGS. 2–7 show one representative embodiment of the hand-held apparatus 100 in accordance with the present invention. As shown in these figures, the hand-held apparatus 100 of the present invention includes a compact housing 10 capable of being held within a hand of an operator. This compact housing 10 preferably allows single-handed operation of the hand-held apparatus 100. For purpose of illustration, the compact housing 10 embodied herein generally is a polyhedron-shaped container configured to contain the various components of hand-held apparatus 100. The compact housing 10 alternatively may be contoured to substantially match the shape of the operator's palm or may be provided with any of a variety of geometric or fanciful shapes. The compact housing 10 likewise may have an open construction that readily allows access and visibility to components provided therein, although a substantially closed construction is preferred to protect the various components of the hand-held apparatus 100.

Regardless of shape, the compact housing 10 preferably is of appropriate size to be grasped single-handedly. The compact housing 10 therefore should have overall dimensions no greater than about 9 inches in length, about 4 inches in width and about 2½ inches in thickness. Preferred dimensions of the compact housing 10, however, are about 6½ inches in length, about 2½ inches in width and about ½ inch in thickness. To minimize expense and weight, the compact housing 10 preferably is constructed of a durable, lightweight material such a plastic or aluminum. This may be accomplished using known manufacturing methods, including stamping, injection molding or pressure drawing techniques.

The data entry pad provided in accordance with the present invention is used for selecting one of the medical calculations stored in the memory of the controller 70, and for entering data required for execution of the selected medical calculation. The data entry pad also is used for validating data entries in response to a request for validation provided by the controller 70, as well as accessing and actuating additional available features such as a chronometer or a data entry override, as will be described.

Figure 2:
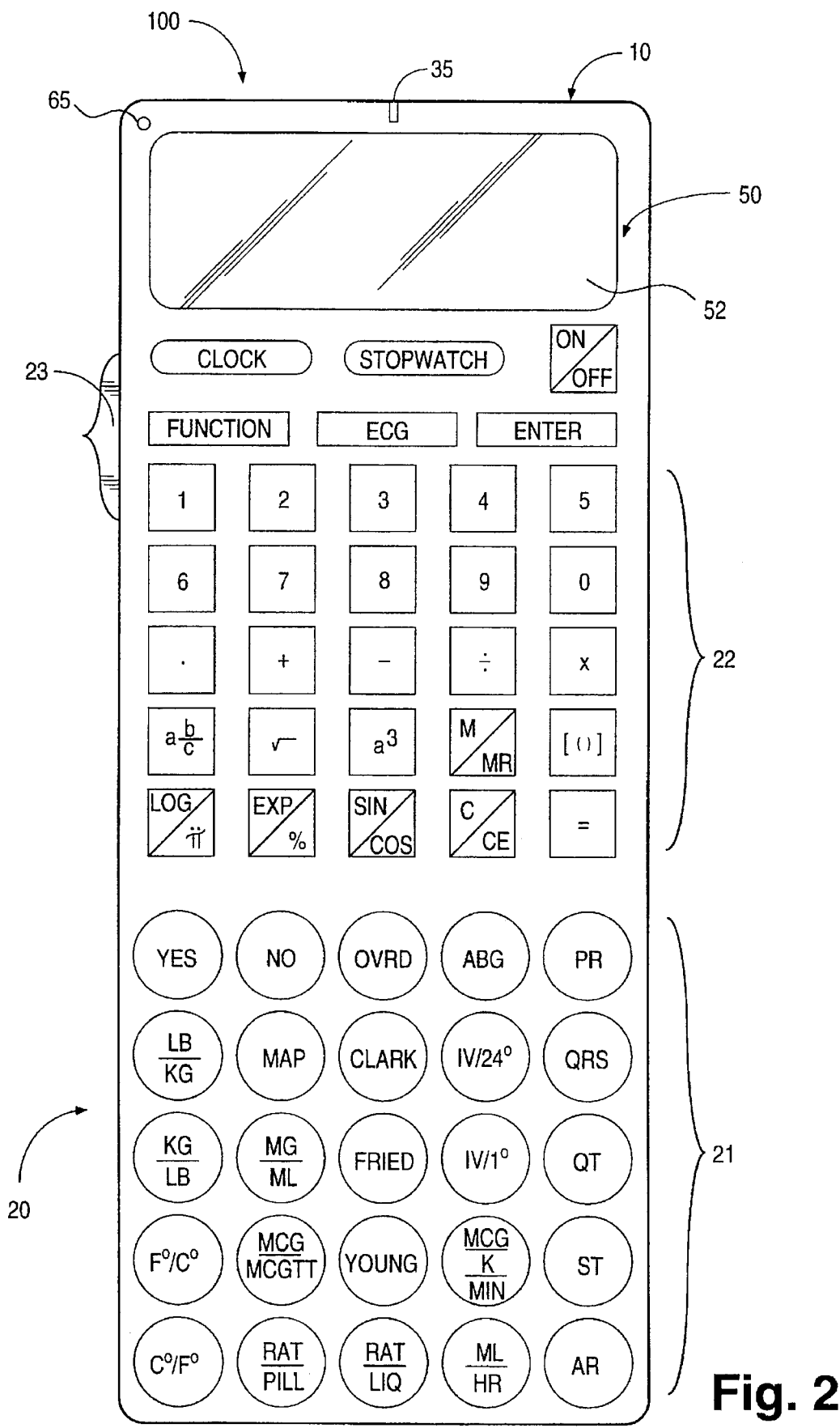
FIG. 2 is a front view of a representative embodiment the hand-held apparatus of the present invention.
Figure 3:
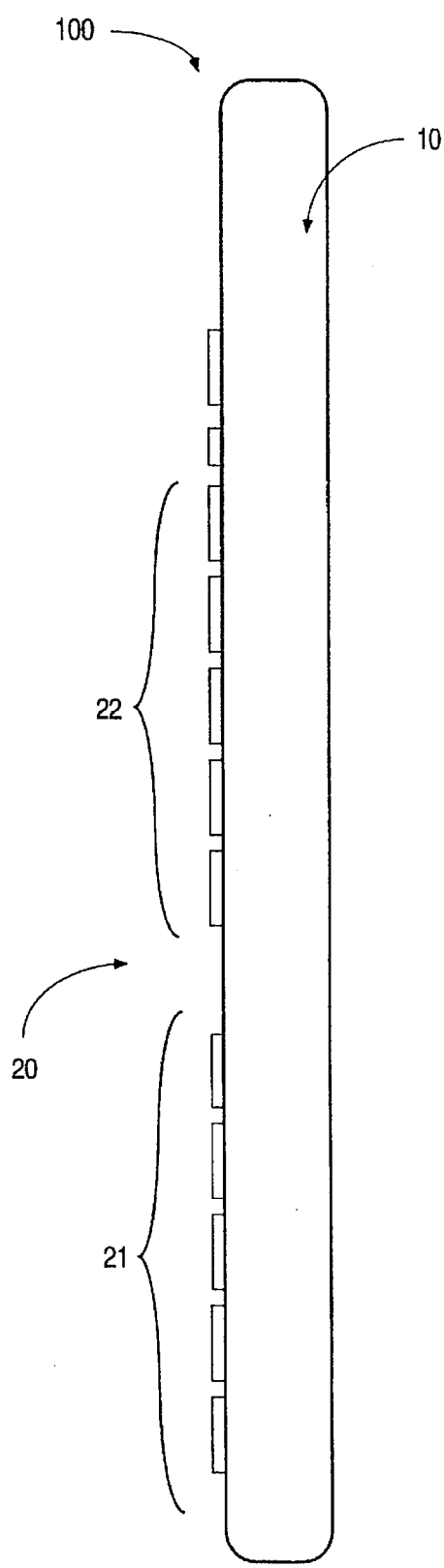
FIG. 3 is a right side view of the hand-held apparatus shown in FIG. 2.
Figure 4:
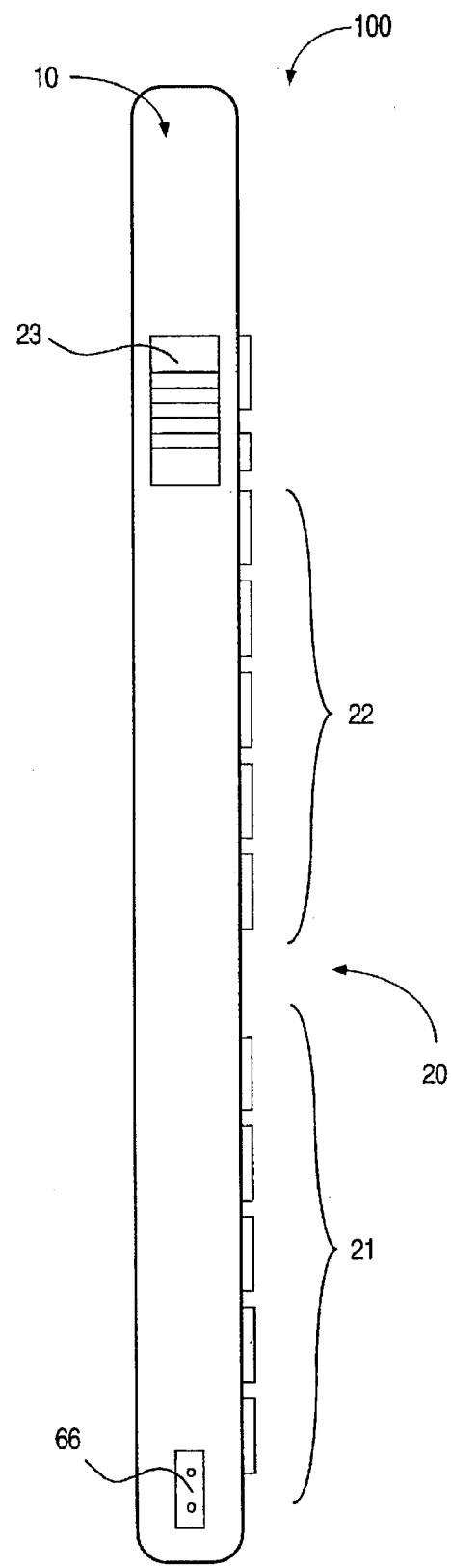
FIG. 4 is a left side view of the hand-held apparatus shown in FIG. 2.

Any of a variety of known data entry devices may be used for the data entry pad. For example, the data entry pad may be a touch screen, a digitizing pen-and-tablet, or even a audio monitor with voice recognition capabilities if a sophisticated construction is desired. For purpose of illustration and not limitation, however, FIGS. 2–7 show the data entry pad 20 of the hand-held apparatus 100 embodied herein as an array of keys located on the front surface of the compact housing 10. These keys may be capacitive type keys, hard-contact type keys or keys of any other known construction. Although the physical configuration and arrangement of these keys may be varied, FIG. 2 shows that the keys of the data entry pad 20 embodied herein generally are divided into two groups.

The first group of keys 21 correspond to the variety of medical calculations that may be selected and performed using the hand-held apparatus 100 of the present invention. Each of these keys offer single key stroke operation for generating a corresponding command signal to select the desired medical calculation quickly and easily. The specific medical calculations offered by these keys will vary depending upon the intended user and application. For example, and for purpose of illustration, the representative hand-held apparatus 100 embodied herein relates to cardiac care. The medical calculations offered by the first group of keys 21 of this embodiment therefore are generally directed to the determination of various cardiac related conditions of a patient, as well as the determination and conversion of medication doses. Additionally, response keys such as [YES] and [NO] keys and an override [OVRD] key also may be provided. Additional keys likewise may be provided to select medical calculations directed to relevant measurements of inputted graphical information, or to request particular information such as time measurements from a chronometer. These various medical calculations and functions are described in greater detail below in conjunction with the controller 70.

The second group of keys 22 generally correspond to the keys of a conventional pocket calculator. These keys include the ten numeric keys [0–9] and a decimal point key [.] for generating data signals corresponding to an entered value. An [ENTER] key also is provided to register the entered data required for execution of the medical calculation selected by the first group of keys 21. Preferably, the second group of keys 22 also includes at least the basic mathematic operation keys [+,−,×,÷] and the equal sign [=] for generating command signals to perform manual calculations. Although not required, additional preferred keys of the second group 22 correspond to percent [%], log [log], cube [$a^3$], square [$a^2$], square root [$\sqrt{}$], pi [$\pi$], sine [sin], cosine [cos], and tangent [tan], which likewise generate command signals to perform associated calculations. Furthermore, memory keys [M+, M−,MC,MR] also may be provided to store or manipulate obtained values; and bracket keys [( )] and [CLEAR] keys may be provided to simplify manual mathematical operations.

Figure 5:
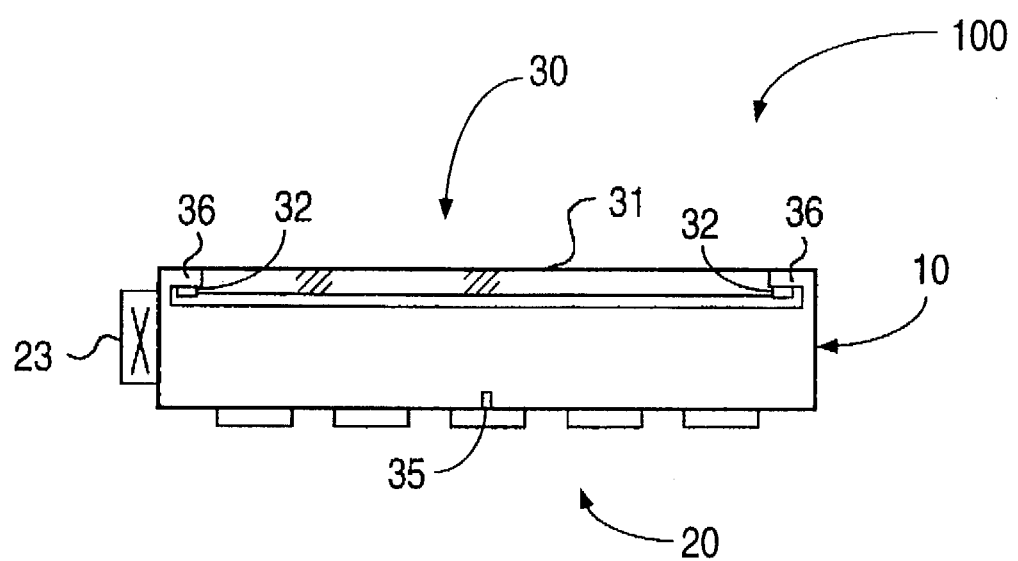
FIG. 5 is a top view of the hand-held apparatus shown in FIG. 2.
Figure 6:
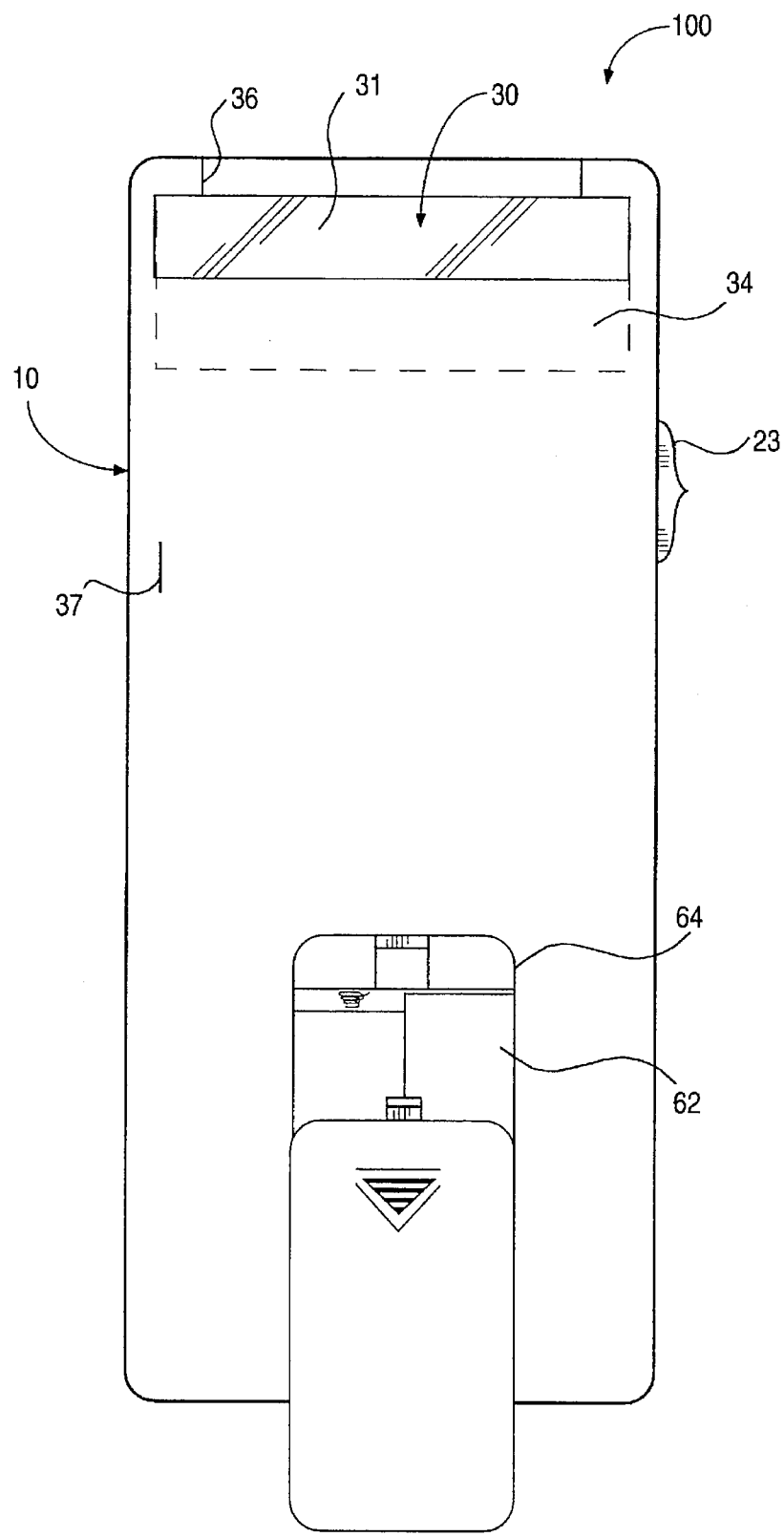
FIG. 6 is a back view of the hand-held apparatus shown in FIG. 2.
Figure 7:
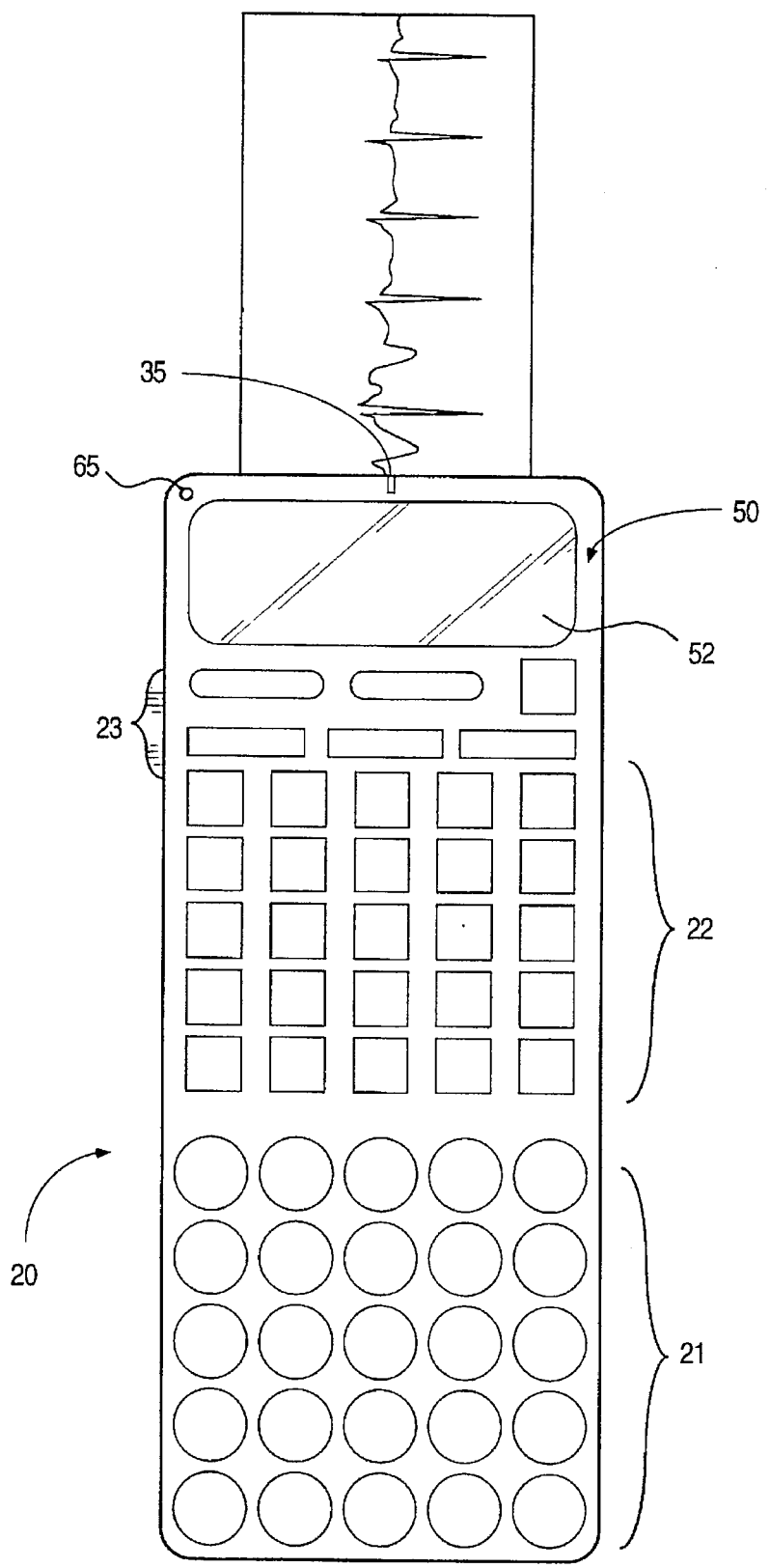
FIG. 7 is the front view of the hand-held apparatus shown in FIG. 2 during input of graphical information.

In addition to the data entry pad 20, and further in accordance with the present invention, the hand-held apparatus 100 also includes an input device of sufficiently compact construction to be provided in the compact housing 10 for inputting graphical information. For example, and as shown in FIGS. 5–7, the input device embodied herein is a scanner 30 including a scanner window 31, wherein the scanner 30 is configured to input graphical information from a substrate sheet that is moved across the scanner window 31. The scanner 30 is activated by an actuation switch 23 provided on the side of the compact housing 10. When activated, the scanner 30 detects the portion of graphical information that is in view through the scanner window 31 using a light-emitting diode and a charge coupled device or similar element, and generates corresponding analog image signals. The analog image signals from the scanner 30 are received by the analog-to digital converter 40 and converted into corresponding machine-readable image data signals. A roller (not shown) or similar member also is provided to detect movement of the substrate sheet across the scanner window 31. As the substrate sheet is moved, the roller indicates the new portions of the graphical information that are obtained so that a complete image may be compiled. Such compact scanners and converters are well known and readily available.

The input of graphical information by the scanner 30 embodied herein is further enhanced by providing a sensor 33 to ensure that the substrate sheet is moved across the scanner window 31 at an appropriate speed. The speed at which the substrate sheet is moved may be evaluated mechanically, such as by monitoring the rotation of the roller, or optically by monitoring uniform markings provided on the substrate sheet, such as the grid pattern of an electrocardiogram strip. When the substrate sheet is moved too quickly or too slowly, an error signal is generated to illuminate an error light or to display a related message on the display 50.

Rather than requiring manual movement of the substrate sheet across the scanner window 31, another aspect of the present invention includes providing a roller 32 or similar element to feed the substrate sheet across the scanner window 31 at a predetermined speed. For example, and as shown in FIG. 5, the hand-held apparatus 100 of the present invention includes a roller 32 located on either side of the scanner window 31 to engage corresponding edges of the substrate sheet. When the scanner 30 is activated by the actuation switch 23, the rollers 32 are rotated by a drive motor or similar device to move the substrate sheet across the scanner window 31 at a predetermined speed.

As shown in FIG. 6, and in accordance with another aspect of the present invention, a moveable cover 34 is provided to protect the scanner window 31 when the scanner 30 is not in use. Particularly, the cover 34 is moveable between a closed position to protect the scanner window 31 and an open position to expose the scanner window 31. In the preferred embodiment, the cover 34 is configured to move automatically to the open position when the scanner 30 is activated. This may be accomplished using a solenoid to move the cover 34 to the open position when the scanner 30 is activated, while providing a spring to bias the cover 34 toward the closed position when the scanner 30 is deactivated. Alternatively, the cover 34 may be spring biased toward the open position. In this manner, the cover 34 is held in the closed position by a mechanical latch that is released when the scanner 30 is activated. After scanning is completed, the cover 34 is manually returned to the closed position.

Figure 16:
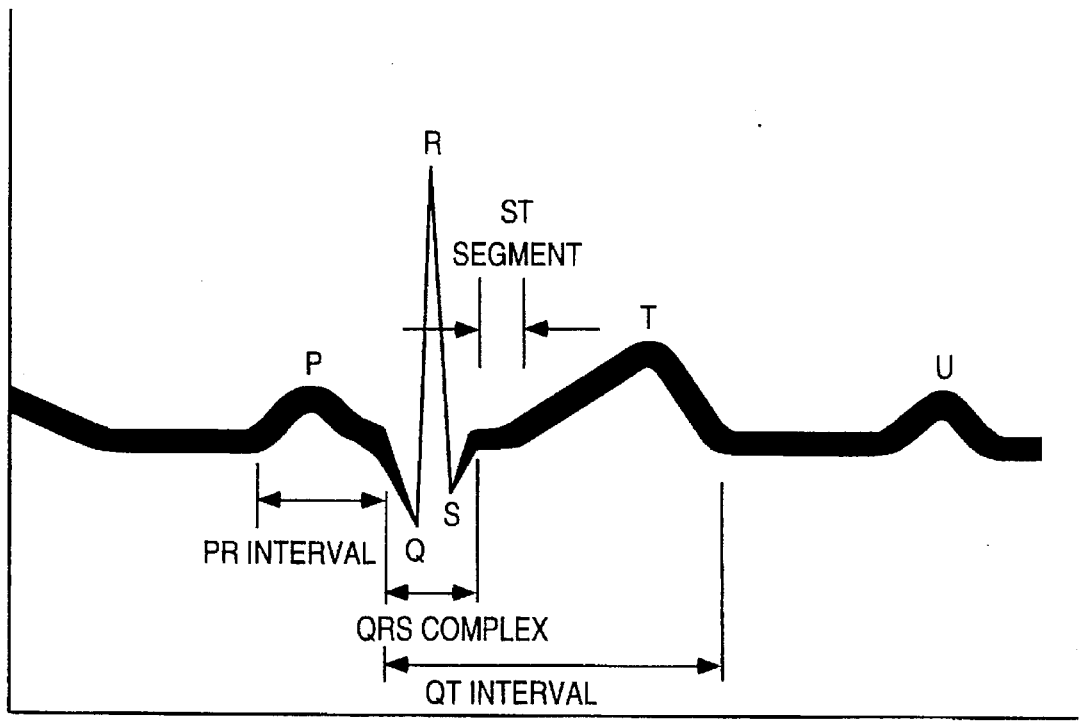
FIG. 16 is a representative electrocardiogram waveform showing various relevant measurements that may be calculated by the hand-held apparatus of the present invention.

Although the scanner 30 may be configured to input a variety of graphical information, the preferred embodiment of the hand-held apparatus 100 of the present invention is configured to input cardiac-related graphical information such as electrocardiogram (ECG) waveforms. ECG waveforms typically are printed on strips of grid substrate by a conventional cardiac monitor or electrocardiograph machine to depict changes in electrical potential that occur throughout a heartbeat relative to a time baseline, as shown in FIG. 16 and described further below. Typically, six inch ECG waveform strips are provided, wherein each inch represents one second. The hand-held apparatus of the present invention therefore is configured to recognize this universal scale; however, a switch (not shown) may be provided to select alternative scales if desired. For example, if an ECG waveform having a scale of 0.5 seconds per inch is provided, the appropriate scale recognized by the hand-held apparatus using the scanner may be selected accordingly.

To further maintain the accuracy of the inputted graphical information, the preferred embodiment of the hand-held apparatus 100 of the present invention also includes a guide 35 located proximate the scanner 30 to ensure proper alignment of the substrate sheet with the scanner window 31. For example, the guide 35 may include a mark or indicia on the compact housing 10 proximate the scanner 30 for proper alignment of the ECG waveform baseline as the substrate sheet is moved across the scanner window 31 as shown in FIG. 7. Tracks 36 likewise may be provided in the compact housing 10 adjacent the scanner window 31 to engage and guide the edges of the substrate sheet. The tracks 36 may be fixed in position as shown in FIGS. 5–6, or adjustable to accommodate substrate sheets of various widths. Additionally, indicia 37 may be provided on the back of the hand-held apparatus as shown in FIG. 6 for the alignment of substrate sheets too large to fit between the tracks 36, such as conventional diagnostic printouts from twelve-lead ECG machines. In this manner, the indicia 37 would correspond to an edge of the larger substrate for alignment with the scanner window 31.

The input device is not limited, however, to the use of a scanner 30. For example, graphical information also may be inputted directly using an external signal port 45 configured to receive image signals from a conventional electrocardiograph machine or similar medical equipment. If provided in analog form, the received image signals would be converted into corresponding image data signals using the analog-to-digital converter 40, as shown in FIG. 1. If the graphical information is input in machine readable form, however, the use of the converter 40 is not necessary.

As noted above, the hand-held apparatus 100 according to the present invention further includes a display 50 provided in the compact housing 10. Particularly, FIG. 2 shows that the display 50 includes a screen 52 located on the front surface of the compact housing 10. A liquid crystal display screen or similar portable display of conventional construction preferably is used. Although the size and capacity of the display 50 may vary, depending on desired resolution and cost of construction, the display 50 is at least sufficiently configured to display the data entered using the data entry pad 20 and the results obtained upon execution of the selected medical calculations. Additionally, and as described in greater detail below, the display 50 also is sufficiently configured to display prompts for required data and requests for validation of entered data that are generated by the controller 70. In the preferred embodiment of the present invention, the display 50 includes a 2½ inch by 1-1/16 inch, monochrome LCD screen capable of displaying two lines of characters with a total of twenty characters per line.

A chronometer 55 also may be included in the compact housing 10 to provide time measurements. Such time measurements include the time of day as provided by a conventional clock, and timed intervals as provided by a stopwatch. The chronometer 55 may be provided as a separate component of the hand-held apparatus 100 or incorporated in either the controller 70 or the display 50. Preferably, separate keys are provided on the data entry pad 20 to access the clock and the stopwatch capabilities, respectively. By providing the chronometer 55 in communication with the display 50, either directly or via the controller 70, each of these time measurements may be displayed on the display screen 52.

Power for the hand-held apparatus 100 preferably is provided from a power supply 60 located in the compact housing 10. FIG. 6 shows a compartment 64 partially opened, which is provided for a battery pack 62. In the preferred embodiment, the battery pack 62 is rechargeable and configured to provide at least eight hours of continuous operation of the hand-held apparatus 100. Terminals 66 also may be provided in the compact housing 10 of the hand-held apparatus 100 for connection with a conventional electrical outlet or similar power source to allow recharging of the battery pack 62, as well as for AC operation via an electrical cord if desired. Alternatively, or additionally, the battery pack 62 may be configured for quick release for placement in a remote electrical recharger. A lithium battery also is provided in the compact housing 10 as a secondary power supply 60 in communication with the controller 70 to maintain stored medical calculations and data, as will be described.

Also provided in the housing 10, as best shown in FIGS. 2 and 7, is an indicator 63 in communication with the power supply 60. The indicator 63 includes an indicator light 65 and a power sensor to determine when power available from the power supply 60 is below a predetermined level. When the available power drops below the predetermined level, a signal is generated by the power sensor to actuate the indicator light 65. Alternatively, the indicator 63 may be provided in communication with the controller 70 so as to generate a signal to display a low power indicator on the display 50. Power for the indicator 63 may be provided from the lithium battery or from another back-up power supply, if desired.

As noted above, and in accordance with the present invention, a controller 70 is provided in the compact housing 10 to execute the selected medical calculations and process the entered data and graphical information. FIG. 1 shows a block diagram of the major components of the apparatus of the present invention. The controller 70 is coupled with the data entry pad 20 to receive the generated data signals and command signals, and is in communication with the scanner 30 and converter 40 to receive the generated image data signals. The controller 70 also is in communication with the display 50. In this manner, data entered using the data entry pad 20 and results obtained upon execution of the selected medical calculations are displayed by the display 50, which is driven by display signals generated by the controller 70. Additionally, prompts for required data and requests for validation of entered data also are displayed by the display 50 in accordance with display signals generated by the controller 70.

Figure 8:
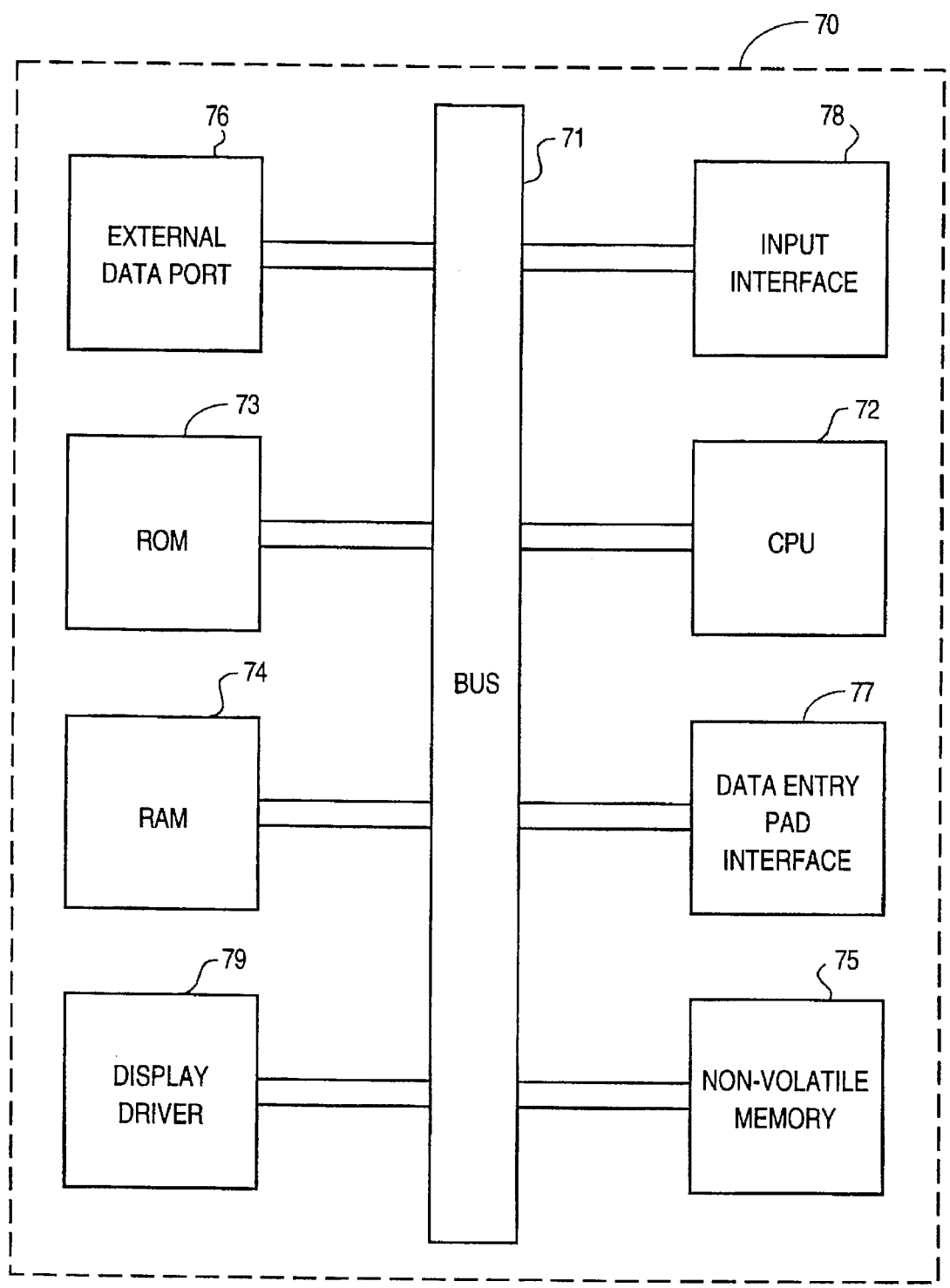
FIG. 8 is a block diagram showing components of the controller shown in FIG. 1.

A block diagram of a representative embodiment of the controller 70 of the present invention is shown in FIG. 8. The controller 70 is provided with a conventional central processing unit (CPU) 72 including a system clock, an arithmetic logic unit and a bus interface unit for communication via bus 71. Although a variety of CPU 72 configurations are readily known and available, the preferred embodiment of the hand-held apparatus 100 of the present invention uses a microprocessor chip configured with sufficient speed and capacity to control the operation of the various components of hand-held apparatus 100. Such microprocessor chips are available from Samsung and Intel. Alternative CPU 72 configurations may be used, however, depending upon the intended demands and desired cost of construction. Alternatively, an application-specific microcontroller may be used.

A read-only memory (ROM) 73 is provided for permanent storage of the basic microprocessor operation instructions and system programs of the hand-held apparatus 100. The controller 70 also uses ROM 73 to store the various medical calculations to be performed using the hand-held apparatus 100 of the present invention stored therein. Examples of such medical calculations are provided below. The ROM 73 may be configured as an integrated circuit, if desired, or provided as a conventional erasable programmable read-only memory (EPROM) of sufficient capacity. Communication between the CPU 72 and the ROM 73 is provided via bus 71. Additionally, the controller 70 includes a random access memory (RAM) 74 in communication with the CPU 72 via bus 71. The RAM 74 is used to store system variables entered using the data entry pad, as well as provide associated memory for operation of the display. The RAM 74 is of sufficient capacity to store the data entered using the data entry pad and image data corresponding to the graphical information inputted by the input device for execution of the selected medical calculations, as well as to store the data required for display.

The CPU 72 is connected via bus 71 to a data entry pad interface 77 to receive and process the command signals and data signals generated by the data entry pad 20. The controller 70 likewise includes an input device interface 78 configured to interface with the scanner 30 and analog-to-digital converter 40 for receipt of the image data signals corresponding to the inputted graphical information. A display driver 79 also is provided to drive the display 50 in accordance with display signals generated by the CPU 72 and received via bus 71. The interfaces and driver are each preferably provided as a conventional chip of appropriate capacity and configuration. If desired, however, an application specific integrated circuit (ASIC) likewise may be used for some or all of these functions.

These various elements of the controller 70 preferably are interconnected on a conventional printed circuit board. Additionally, the preferred embodiment of the controller 70 also includes an external data port 76 in communication with the CPU 72 via the bus 71. In this preferred embodiment, the results obtained upon execution of the selected medical calculations may be downloaded to an external apparatus such as a personal computer or computer system for subsequent use if desired. As such, a secondary memory preferably is provided to store these results until downloading is possible. The secondary memory preferably is non-volatile memory 75 powered by the lithium battery, such as a separate chip of sufficient storage capacity to store the results of medical calculations performed during a typical eight hour interval.

The configuration of the controller 70 is further understood with reference to the operation of the hand-held apparatus 100 of the present invention. As noted above, a command signal is generated by the data entry pad 20 corresponding to the selection of a medical calculation using the keys of the first group 21. Upon receipt of the command signal from the data entry pad 20 via the data entry pad interface 77, the controller 70 is configured to retrieve the selected medical calculation from the ROM 73. In accordance with the present invention, the controller 70 likewise is configured to provide a prompt for entry of data required for execution of the selected medical calculation. That is, a prompt is provided by the controller 70 for each variable associated with the selected medical calculation. Each prompt is provided as a display signal that is communicated to the display 50 via the display driver 79 for display of the prompt.

Execution of the selected medical calculation is continued after entry of the requested data. Prior to providing the results of the executed medical calculations, however, and further in accordance with the present invention, the controller 70 provides a request for validation of each data entry made using the data entry pad 20. As with the prompt for data entry, the request for validation is provided as a display signal that is communicated to the display 50 via the display driver 79 for display of the request. A corresponding request for validation is provided for each data entry made using the data entry pad 20. After all data entries have been entered and validated, the controller 70 displays the results of the executed medical calculation on the display 50 by generating a corresponding display signal.

For purpose of illustration and not limitation, reference now is made to the logic flow diagrams for several examples of representative medical calculations performed using the hand-held apparatus 100 of the present invention. The following examples demonstrate medical calculations associated with cardiac care that require the entry of one or more variables. Some examples include intermediate calculations that are performed between the entry of data; others require all data entry prior to performing the selected calculation. Each example includes, however, the validation of each data entry made using the data entry pad 20. Although reference is made to specific medical calculations, these examples are not exclusive of the medical calculations that may be performed using the hand-held apparatus 100 of the present invention.

MEDICAL CALCULATIONS HAVING ONE DATA ENTRY

Figure 9:
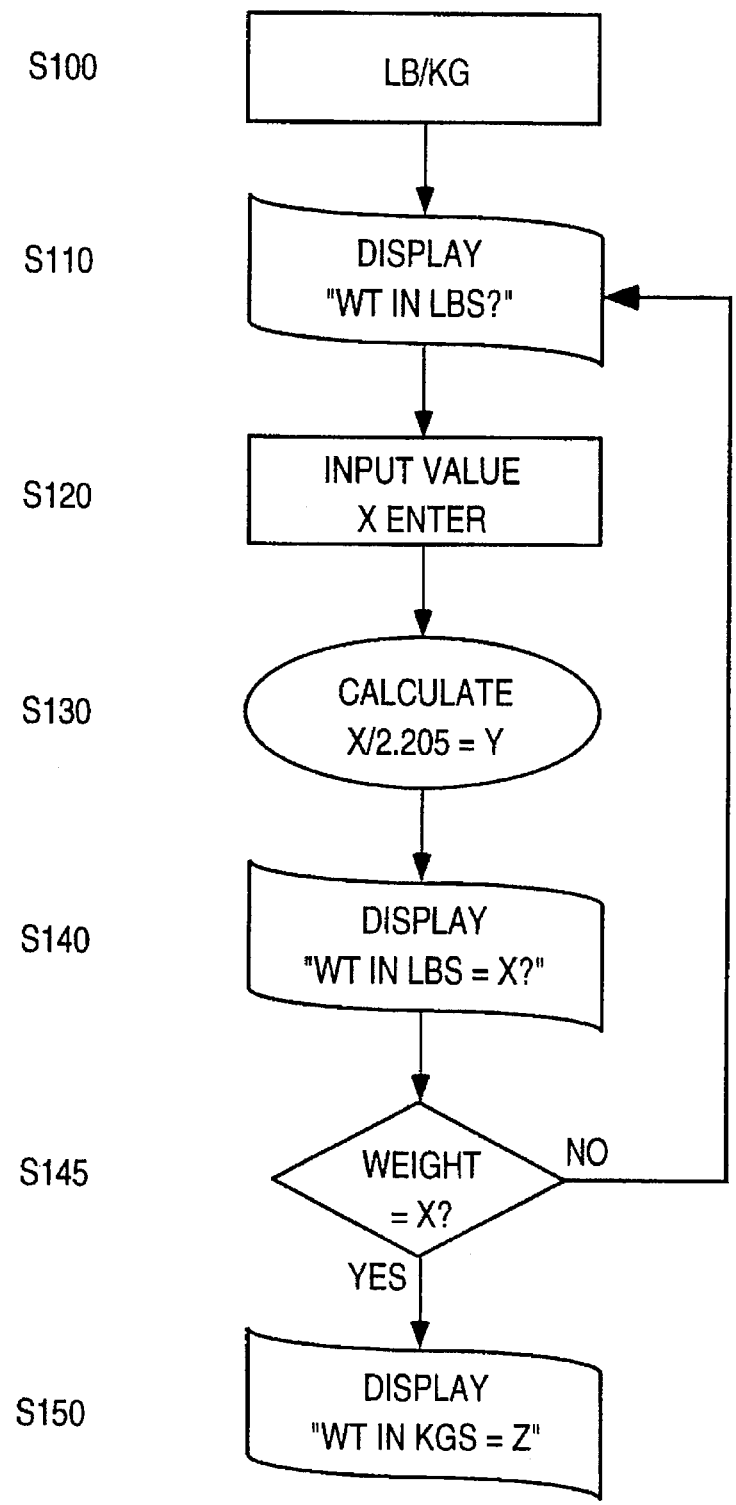
FIG. 9 is a flow diagram showing the logic flow process used for performing a representative medical calculation having one data entry.

FIG. 9 shows a logic flow process performed by the hand-held apparatus 100 of the present invention corresponding to the execution of a medical calculation having only one required data entry. This example demonstrates, as shown in step S100, that the medical calculation for converting pounds to kilograms is selected using the [LB/KG] key on the data entry pad 20. After retrieving the corresponding medical calculation from the memory, the prompt "WT IN LBS?" is displayed on the display 50 in accordance with a display signal generated by the controller 70 as shown by step S110. The appropriate value of weight in pounds is entered using the data entry pad 20 and registered by the [ENTER] key, as shown by step S120. For example, assume the operator enters "125" using the data entry pad 20. Once entered, the selected medical calculation is executed by the controller 70 as shown in step S130 of FIG. 9 to obtain the appropriate result of weight in kilograms. Prior to displaying the obtained results, however, the request for validation is displayed on the display 50 in accordance with a display signal generated by the controller 70 as shown by step S140. In this example, "WT IN LBS=125" would be displayed. If this is incorrect, the operator enters "no" at step S145 by activating the [NO] key on the data entry pad 20. As a result, the controller 70 returns to step S110 of the logic flow process so as to again provide a prompt for weight in pounds by displaying "WT IN LBS?" on the display 50. If this is correct as indicated by the [YES] key, however, the controller 70 displays the results obtained by the executed medical calculation. In this example, "WT IN KGS=56.69" would be displayed.

Similar logic flow processes, using different calculations in step S130, are used by the hand-held apparatus 100 of the present invention to convert weight in kilograms to pounds using the [KG/LB] key; to convert temperature in degrees fahrenheit to degrees Celsius using the [°F./°C.] key; and to convert temperature in degrees Celsius to degrees fahrenheit using the [°C./°F.] key. The calculations that would be performed in step S130 are well known and need not be repeated here.

MEDICAL CALCULATIONS HAVING TWO DATA ENTRIES

Figure 10:
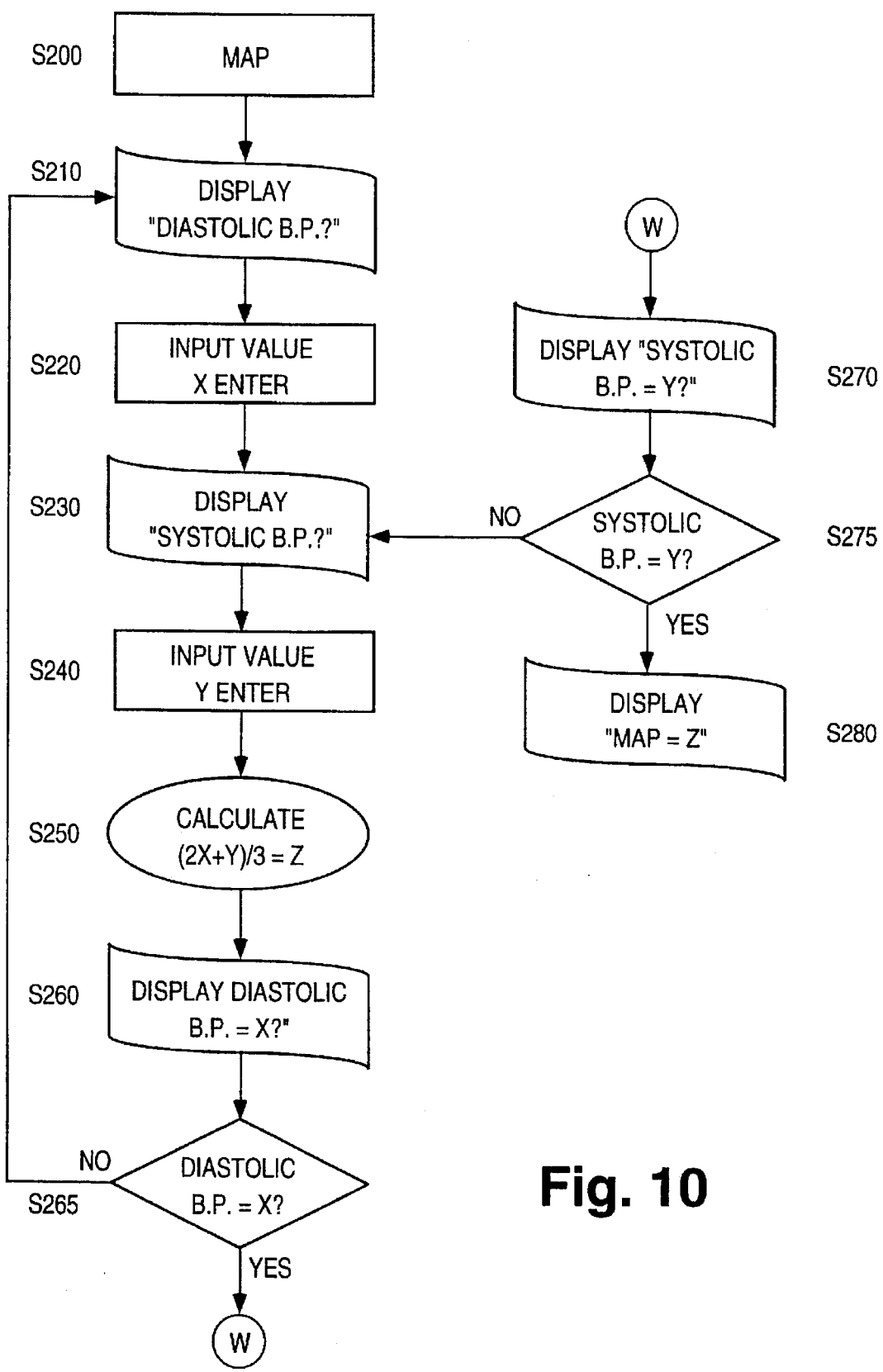
FIG. 10 is a flow diagram showing the logic flow process used for performing a representative medical calculation having two data entries.

FIG. 10 shows a logic flow process performed by the hand-held apparatus 100 of the present invention corresponding to the execution of a medical calculation having two required data entries. Particularly, this example demonstrates the determination of mean arterial pressure base on diastolic blood pressure and systolic blood pressure, as selected using the [MAP] key as shown in step S200. After retrieving the corresponding medical calculation from the memory, the prompt "DIASTOLIC B.P.?" is displayed on the display 50 in accordance with a display signal generated by the controller 70 as shown by step S210. The appropriate value for the diastolic blood pressure is entered using the data entry pad 20 and registered by the [ENTER] key, as shown by step S220. Likewise the prompt "SYSTOLIC B.P.?" is displayed in step S230 and the response is entered in step S240. Once entered, the selected medical calculation is executed by the controller 70 in step S250 to determine the mean arterial pressure. As with the logic flow process of FIG. 9, appropriate requests for validation are displayed in steps S260 and S270 for each data entry made using the data entry pad 20 prior to displaying the obtained results. If either displayed request for validation is indicated as being incorrect in steps S265 and S275, respectively, the controller 70 returns to the corresponding prompt for data entry. Once both data entries are validated, the obtained results are displayed as shown in step S280.

A similar logic flow process, using a different calculation in step S250, is used by the hand-held apparatus 100 of the present invention to determine the amount of drug in milligrams contained in each milliliter of solution, as selected using the [MG/ML] key. Particularly, the first prompt would request "AMOUNT OF DRUG (MG)?", the second prompt would request "AMOUNT OF SOLUTION (ML)?" and the calculation performed would be the division of the first data entry by the second data entry. Similarly, this logic flow process is used to determine the amount of drug in milligrams contained in a microdrop of solution using the [MCG/MCGTT] key, wherein the same prompts are displayed requesting "AMOUNT OF DRUG (MG)?" and "AMOUNT OF SOLUTION (ML)?" and the calculation performed is the product of 16.67 and the first data entry divided by the second data entry.

A logic flow process similar to that of FIG. 10 also is used to determine the number of pills to be administered based on the amount of drug prescribed and the known drug contents of a pill by using the [RAT/PILL] key. Particularly, the first prompt would request "DOSE ORDERED?", the second prompt would request "DOSE PER PILL?", and the calculation performed would be the division of first data entry by the second data entry. Likewise, this logic flow process is used to determine the pediatric dose to be administered proportional to the child's weight in accordance with Clark's rule using the [CLARK] key. The first prompt would request "WT IN LBS?", the second prompt would request "ADULT DOSE?" and the calculation performed would be the product of the first entry and the second entry, divided by 150.

Figure 11:
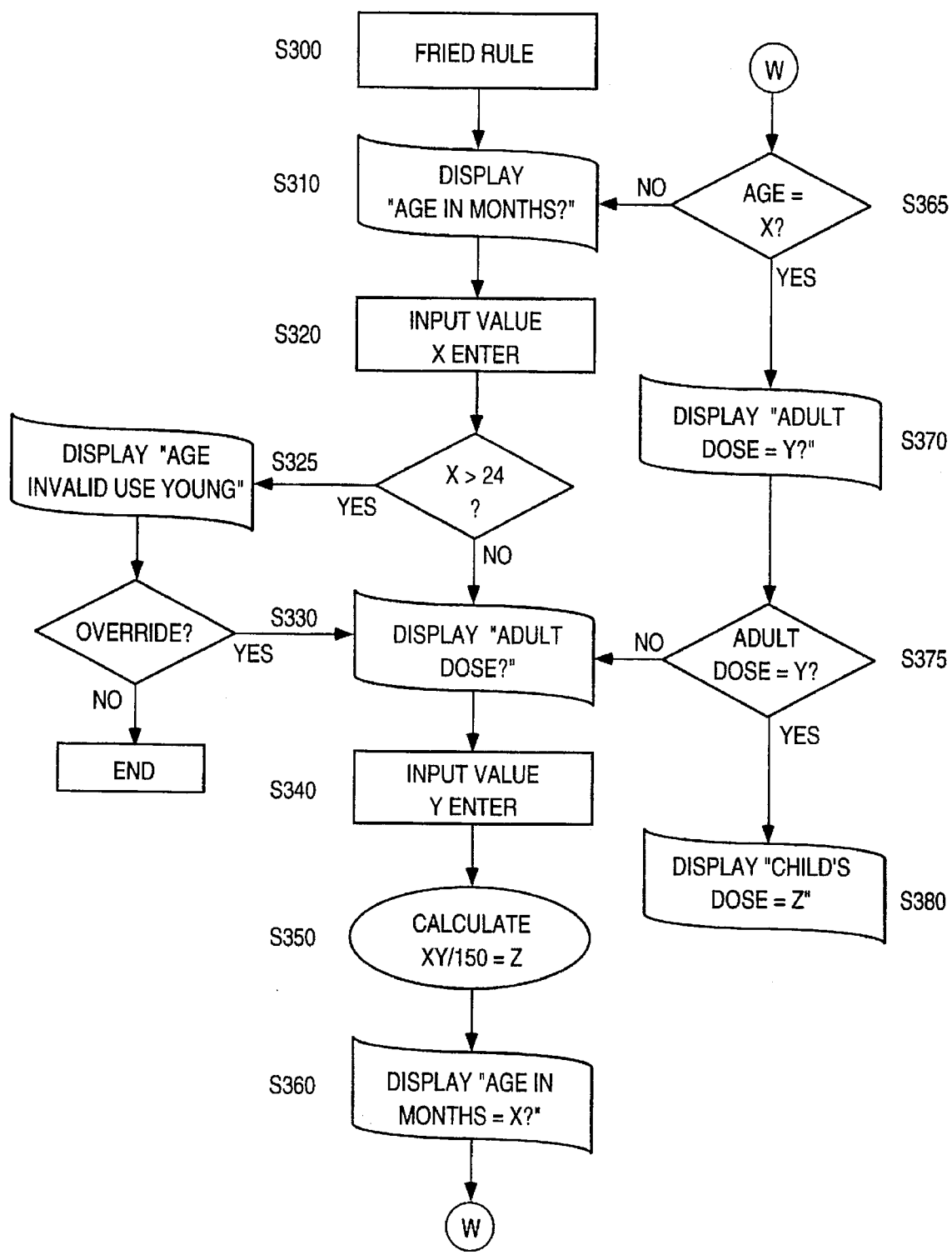
FIG. 11 is another flow diagram showing the logic flow process used for performing a representative medical calculation having two data entries, wherein one data entry is automatically evaluated for inaccuracy.

Another logic flow process corresponding to the execution of a medical calculation having two required data entries is shown in FIG. 11. Particularly, this example demonstrates the determination of a pediatric dose for a child under two years of age in accordance with Fried's rule using the [FRIED] key. In addition to providing prompts for "AGE IN MONTHS?" and "ADULT DOSE?" in steps S310–S340, this logic flow process also includes step S325 to identify automatically when a data entry is invalid. That is, after receiving the data entered in step S320, the controller 70 automatically determines whether the entered data exceeds the expected value. If the value is exceeded, the controller 70 generates a display signal to display an error message or a request for re-entry of the data on the display 50. If the value is not exceeded, the controller 70 continues with the remainder of the selected medical calculation by determining the product of the first entry and the second entry and then dividing by 150 in step S350. Likewise, the [OVRD] key may be used to override this error message and continue with the remainder of the selected calculation. A logic flow process similar to that of FIG. 11 also is used for the determination of a pediatric dose in accordance with Young's rule using the [YOUNG] key. That is, the first prompt requests "AGE IN YEARS?" and an error message is generated if the entered age in years is less than two. If the entered age is greater than or equals two, then the second prompt requests "ADULT DOSE?" and the calculation performed is the product of the first and second entries divided by the sum of 12 and the first entry.

Figure 12A:
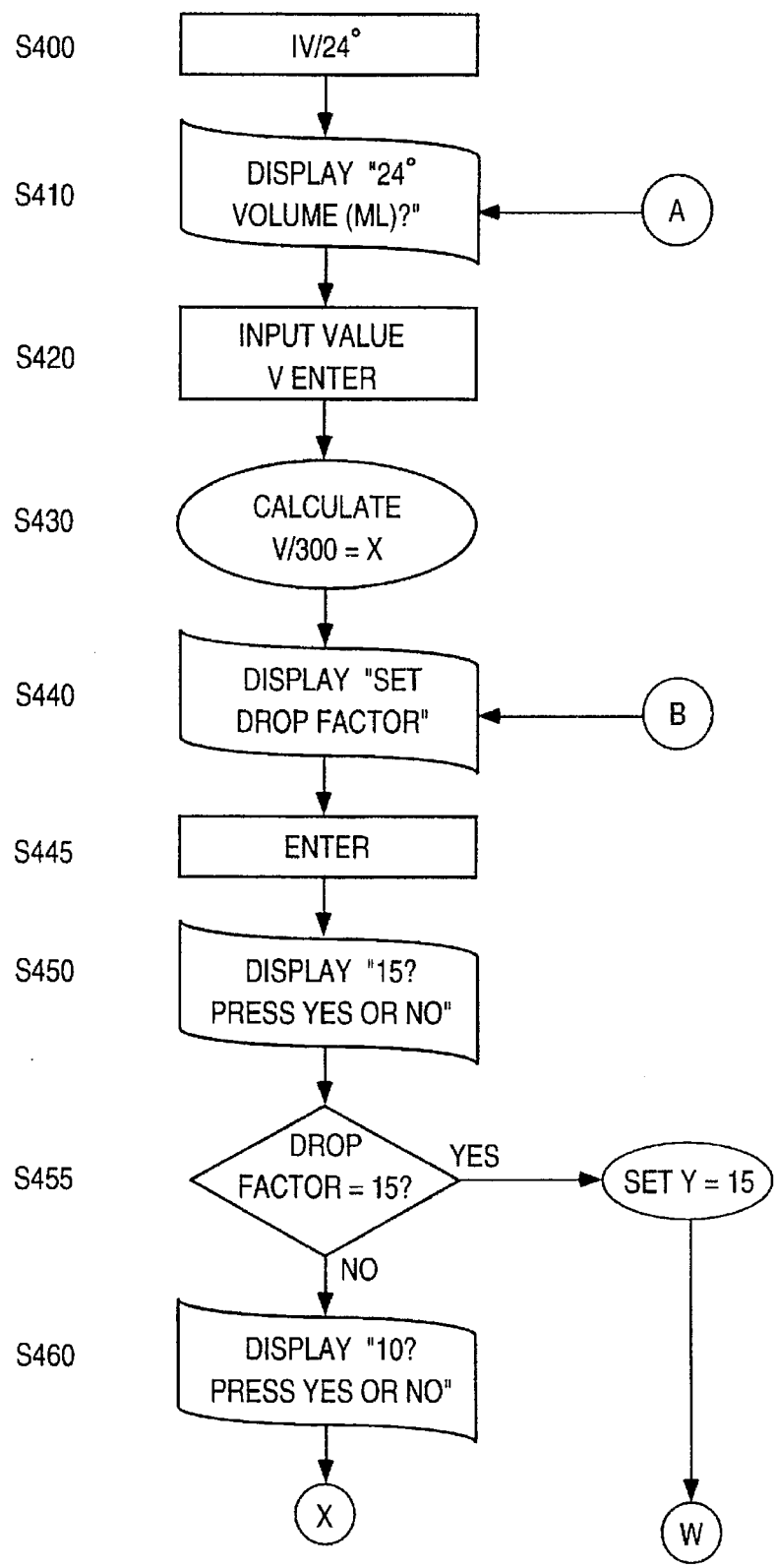
FIGS. 12A–12B is another flow diagram showing the logic flow process used for performing a representative medical calculation having two data entries, wherein predetermined values are provided for selected data entry.
Figure 12B:
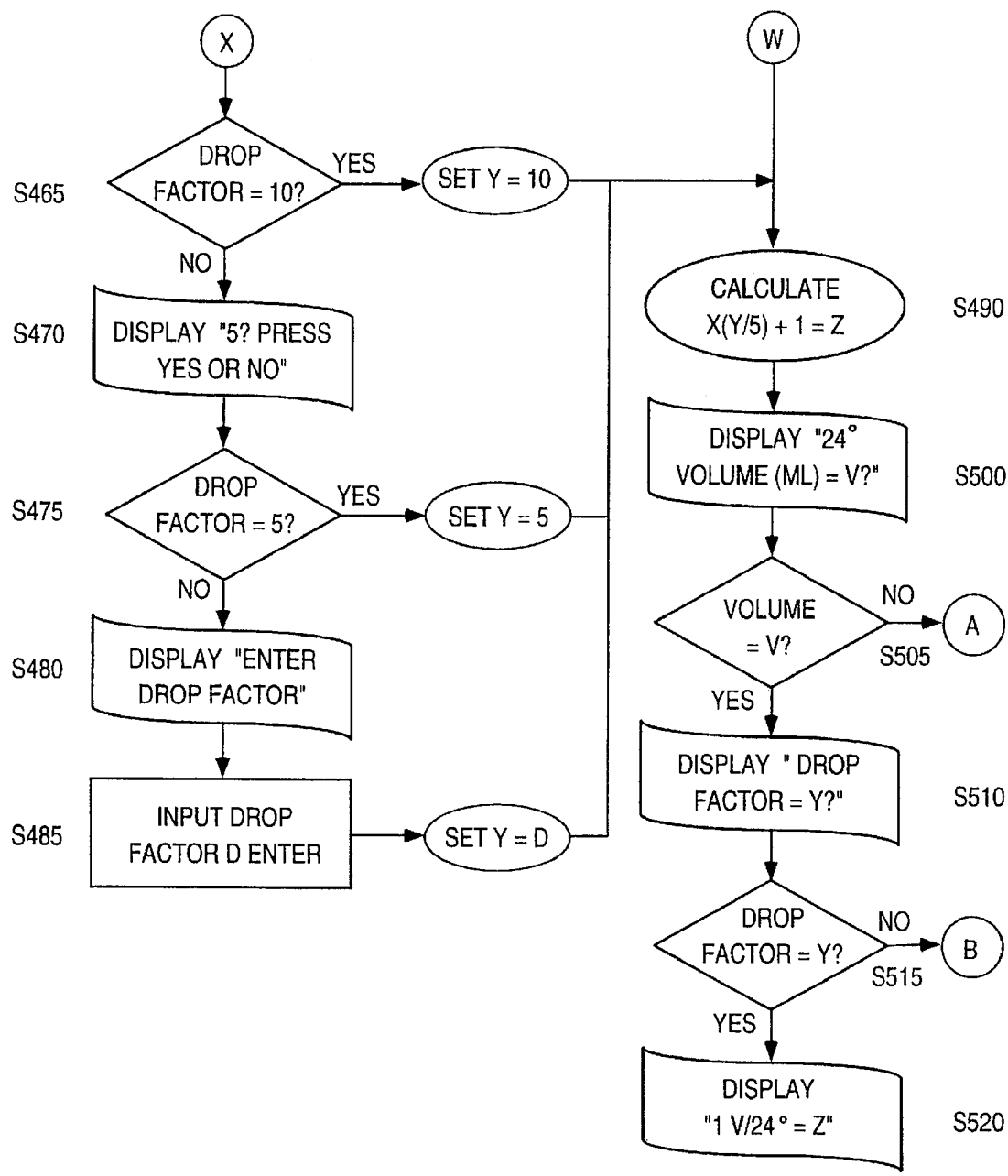

FIGS. 12A–12B show another logic flow process performed by the hand-held apparatus 100 of the present invention corresponding to the execution of a medical calculation having two required data entries. Particularly, this example demonstrates the medical calculation for determining the intravenous flow rate in drops per minute based on a prescribed volume for a 24 hour period selected using the [IV/24°] key as shown in step S400. After retrieving the corresponding medical calculation from the memory, the prompt "24° VOLUME (ML)?" is displayed on the display 50 in accordance with a display signal generated by the controller 70 as shown by step S410. The appropriate value of volume in milliliters is entered using the data entry pad 20 and registered by the [ENTER] key, as shown by step S420. Once entered, a portion of the selected medical calculation is executed by the controller 70 in step S430 and the prompt "SET DROP FACTOR" is displayed in step S440. In response to this prompt, the operator uses the [ENTER], [YES] and [NO] keys to display and select one of three predetermined drop factors as shown steps S445–S475 of FIGS. 12A–12B. If none of the three predetermined drop factors is selected, the controller 70 provides the prompt "ENTER DROP FACTOR" in step S480 for manual entry of the appropriate drop factor using the data entry pad 20 in step S485. Once the drop factor is entered and set, the logic flow process performed by the controller 70 further includes completing the selected medical calculation in step S490, validating each of the data entries in steps S500–S515, and displaying the results obtained by the executed medical calculation in step S520.

A similar logic flow process is used to determine the intravenous flow rate in drops per minute based on a prescribed volume for a one hour period using the [IV/1°] key. When this medical calculation is selected, the first prompt is "VOLUME (ML)/HR?", the second prompt is "SET DROP FACTOR" and the calculation performed is the product of the first entry and the second entry, divided by 60.

MEDICAL CALCULATIONS HAVING MULTIPLE DATA ENTRIES

The hand-held apparatus 100 of the present invention likewise is not limited to performing medical calculations having only two variables. Using the principles demonstrated above by the various logic flow processes for medical calculations having two variables, similar logic flow processes may be configured to execute stored medical calculations having three or more variables.

Figure 13:
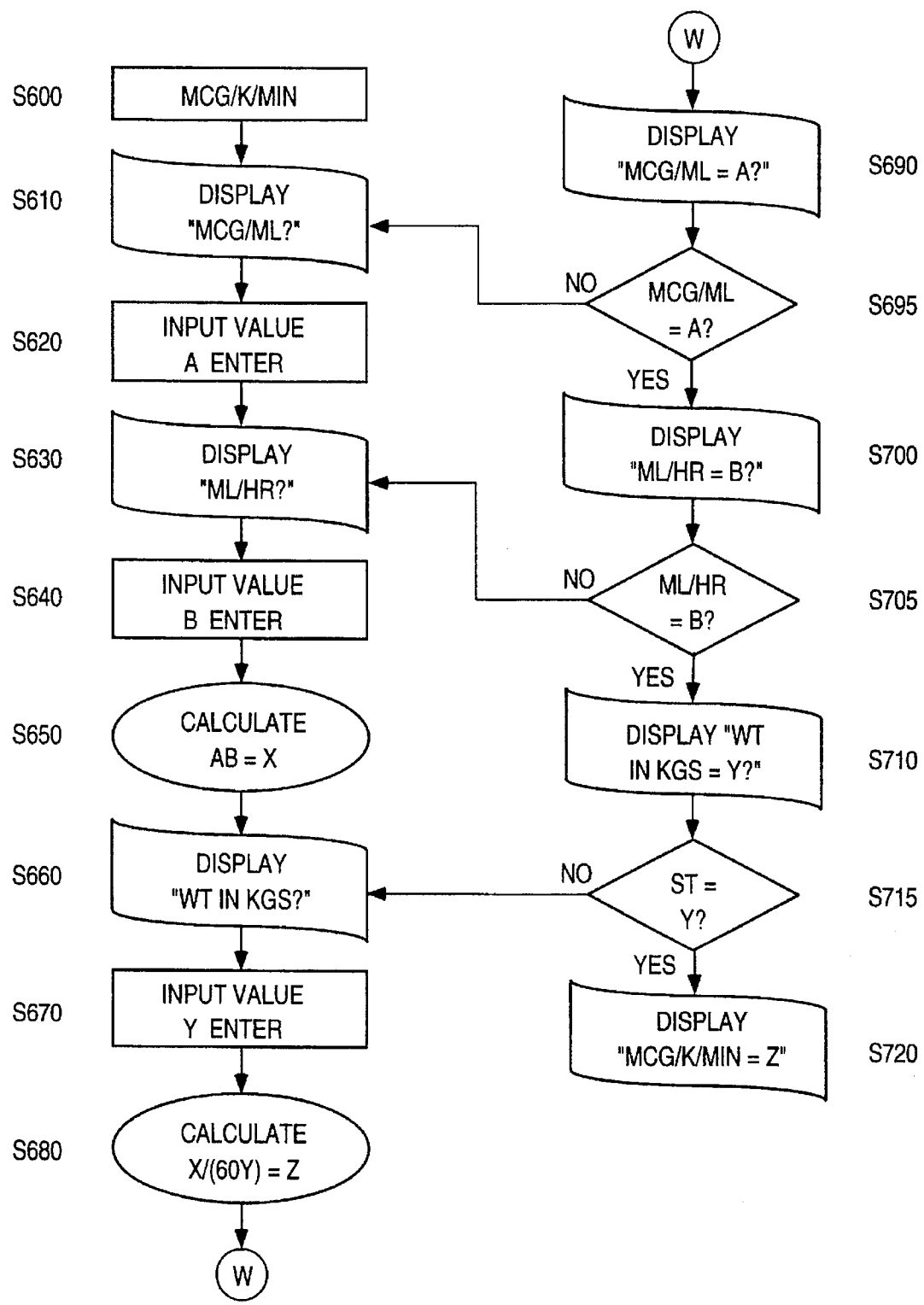
FIG. 13 is a flow diagram showing the logic flow process used for performing a representative medical calculation having three data entries.

For example, FIG. 13 shows a logic flow process performed by the hand-held apparatus 100 of the present invention corresponding to the execution of a medical calculation having three required data entries. Particularly, this example demonstrates the medical calculation for determining a prescribed dose in microdrops to be infused per kilogram per minute based on a known flow rate in milliliters per hour, as selected using the [MCG/K/MIN] key in step S600. Generally, this logic flow process is similar to that shown in FIG. 10. After prompting the two data entries and performing a portion of the selected calculation as shown in steps S610–S650, however, the logic flow process performed by the controller 70 further includes providing a prompt for a third data entry, step S660; entering the required data, step S670; completing the medical calculation, step S680; and then validating each of the three data entries prior to displaying the results obtained from the executed medical calculation, steps S690–S720.

A similar logic flow processes likewise is used to determine a prescribed dose in milliliters per hour to be administered if the amount of microdrops to be infused per kilogram per minute is known using the [ML/HR] key. In this manner, the first prompt is "MCG/KG/MIN?", the second prompt is "WT IN KGS?", the third prompt is "MCG/ML OF SOL?" and the calculation performed is the product of the first two data entries multiplied by 60 and divided by the third data entry. Likewise, this logic flow process is used to determine the amount of an available solution to be administered based upon the prescribed amount of an unavailable solution of a different strength using the [RAT/LIQ] key, wherein the first prompt is "DOSE ORDERED?", the second prompt is "QUANTITY OF LIQUID?", the third prompt is "DOSE IN LIQUID?" and the calculation performed is the product of the first two data entries divided by the third data entry.

MEDICAL CALCULATIONS USING NOMOGRAMS

In addition to executing mathematical formulae, the medical calculations performed by the hand-held apparatus 100 of the present invention also include interpreting nomograms to identify conditions or results corresponding to entered data. That is, the various relationships between the variables of the nomogram are stored in the memory of the controller 70. Alternatively, the various known formulae that compose the nomogram may be stored in the memory of the controller 70. Upon selection of the medical calculation directed to the nomogram, the controller 70 is configured to provide a prompt for each data entry required for interpretation of the nomogram. Once all required data entries have been made using the data entry pad 20, the controller 70 is configured to interpret the entered data relative to the stored relationships or by using the stored formulae to determine the corresponding condition or result. Prior to displaying the result obtained using the stored relationships of the nomogram, the controller 70 further is configured to provide a request for validation of each data entry made using the data entry pad 20. The obtained result is displayed after each data entry is validated.

Figure 14:
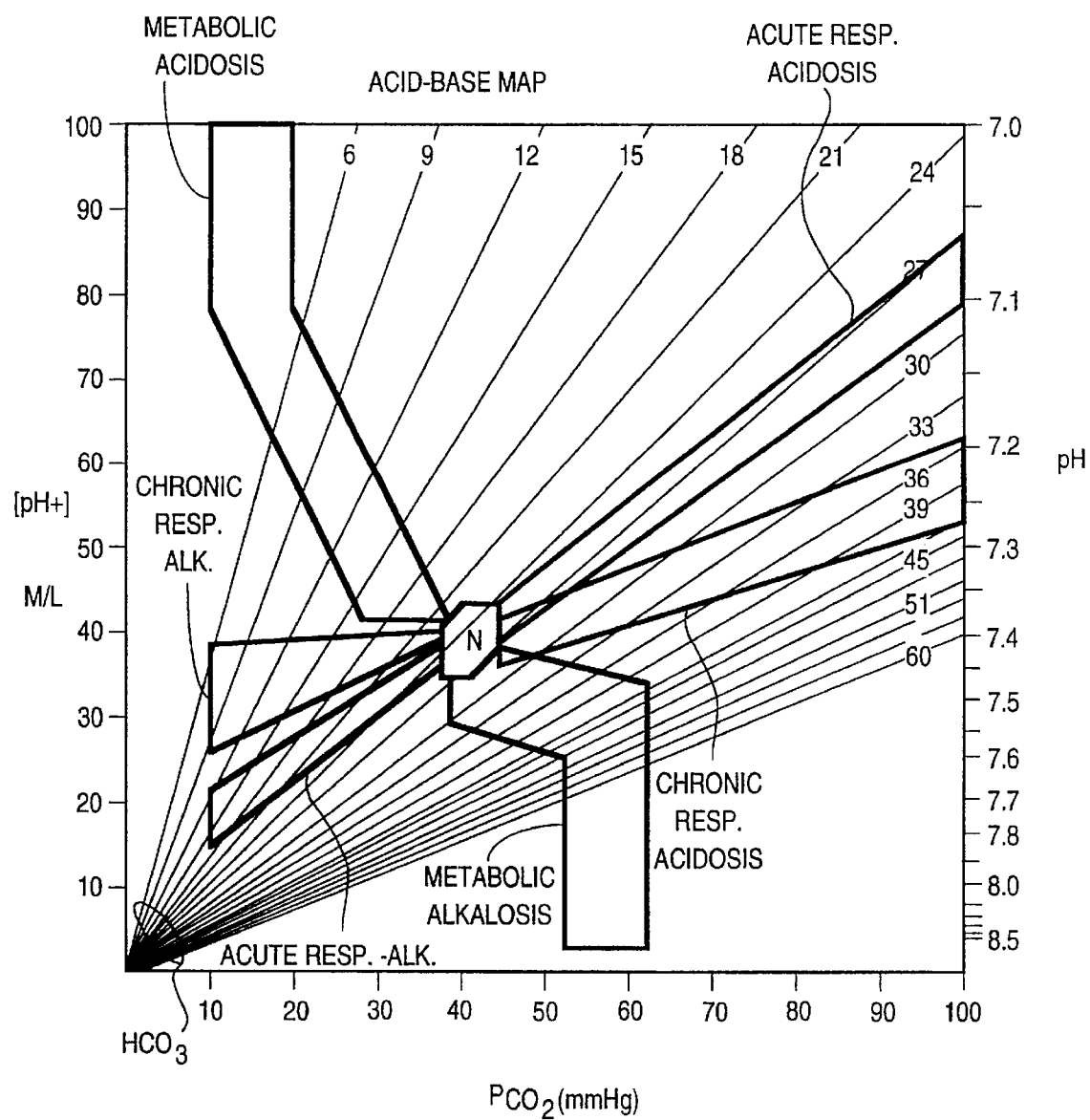
FIG. 14 is a representative nomogram showing known relationships that may be stored in the memory of the controller to calculate a condition based upon data entered.
Figure 15A:
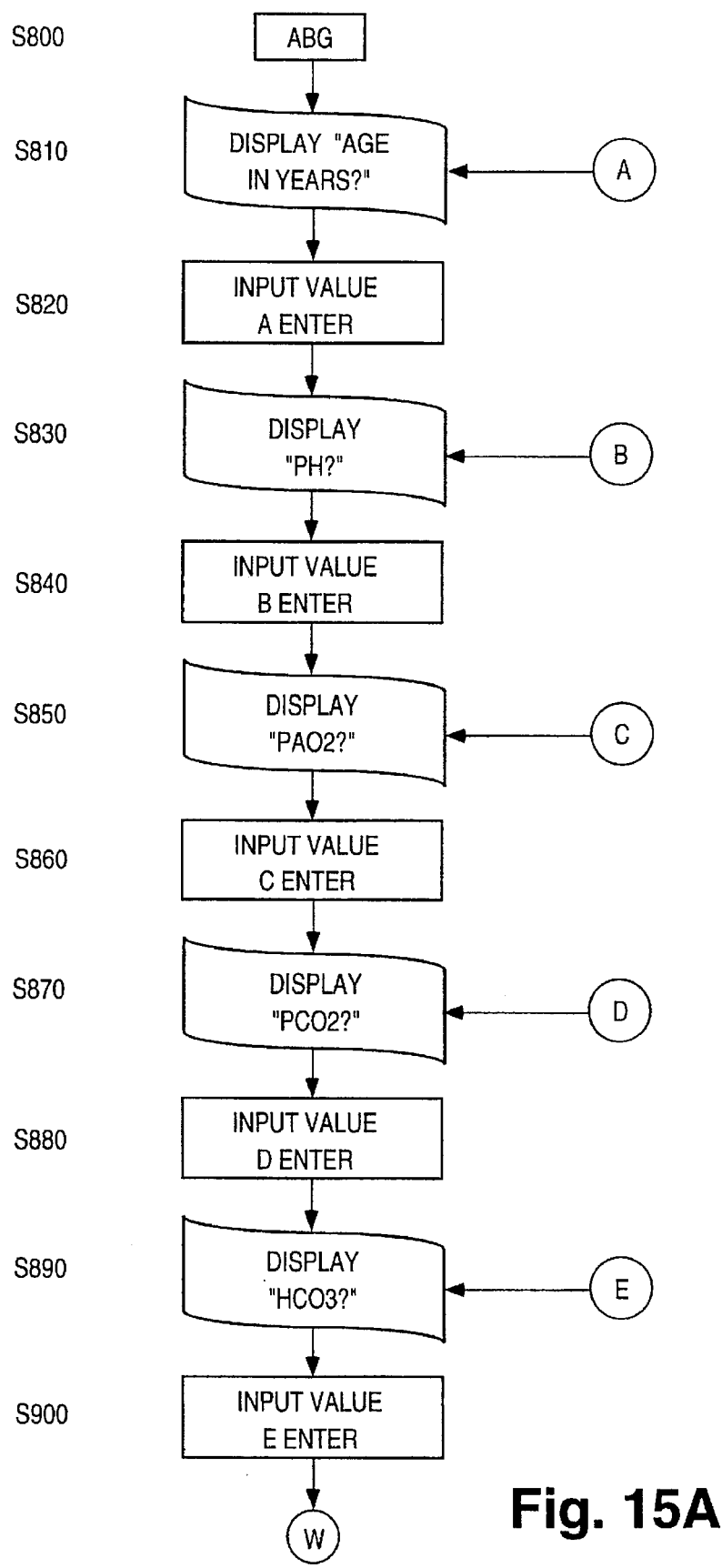
FIGS. 15A–15D is a flow diagram showing the logic flow process used for performing a medical calculation based on the nomogram of FIG. 14.
Figure 15B:
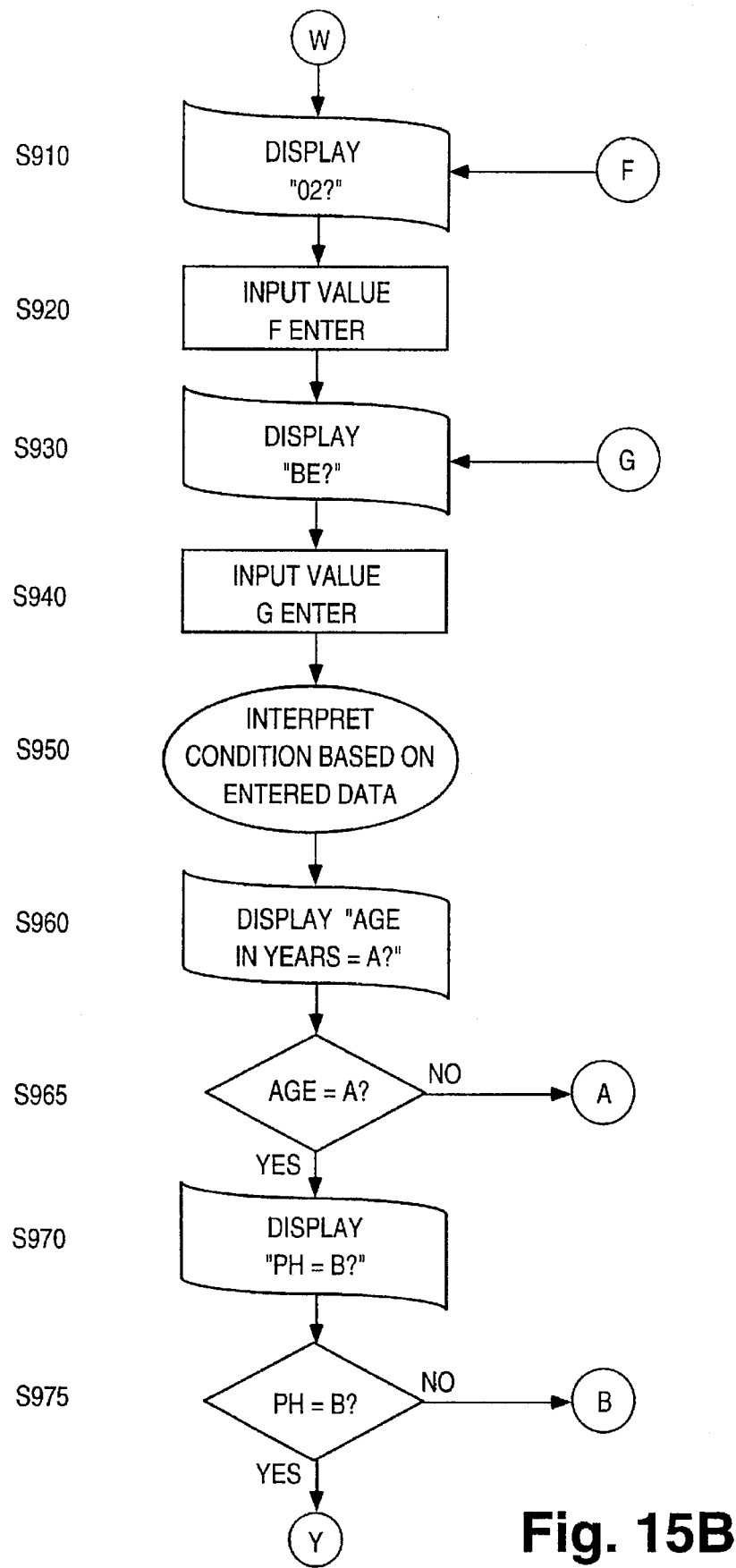
Figure 15C:
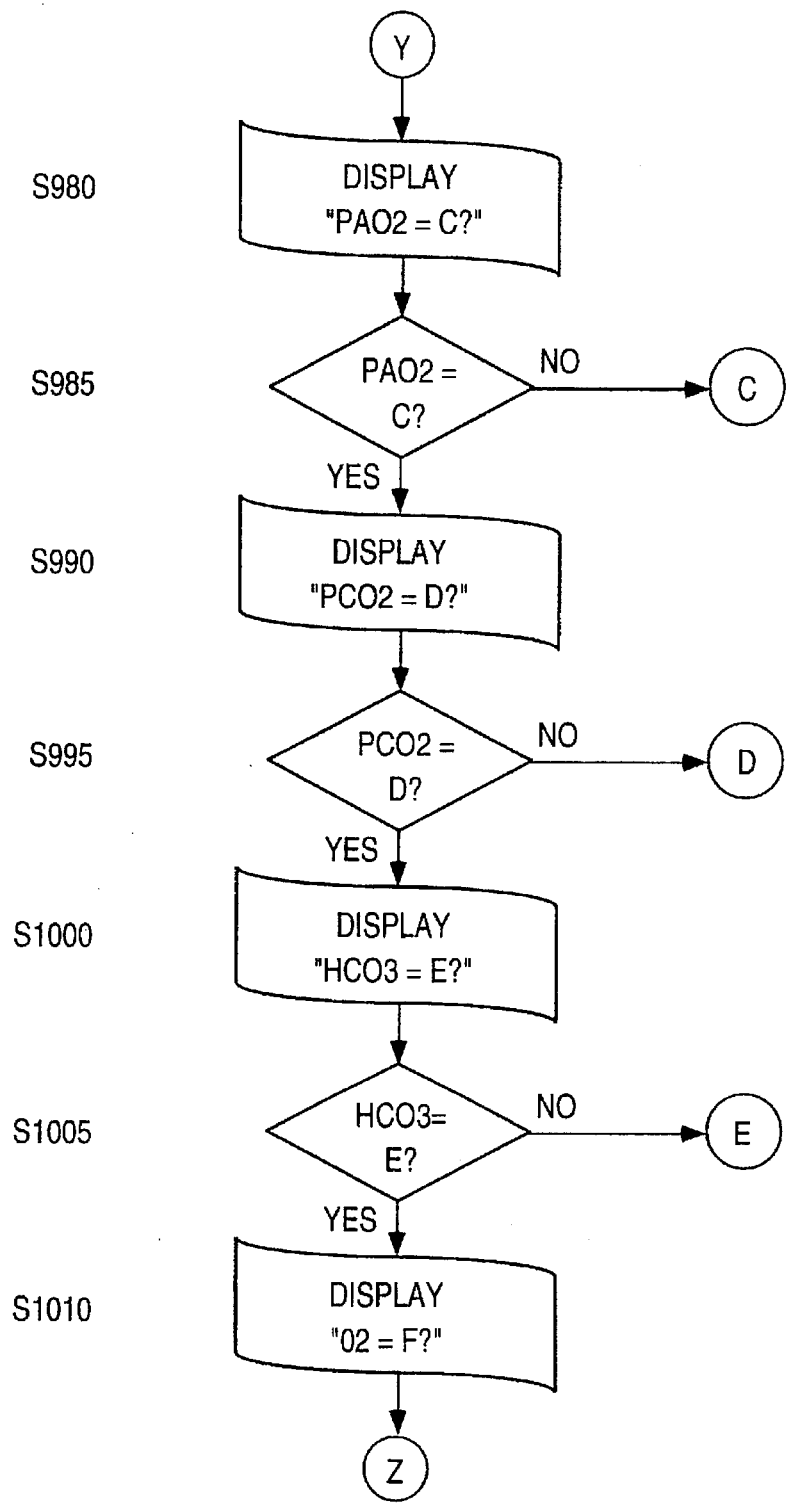
Figure 15D:
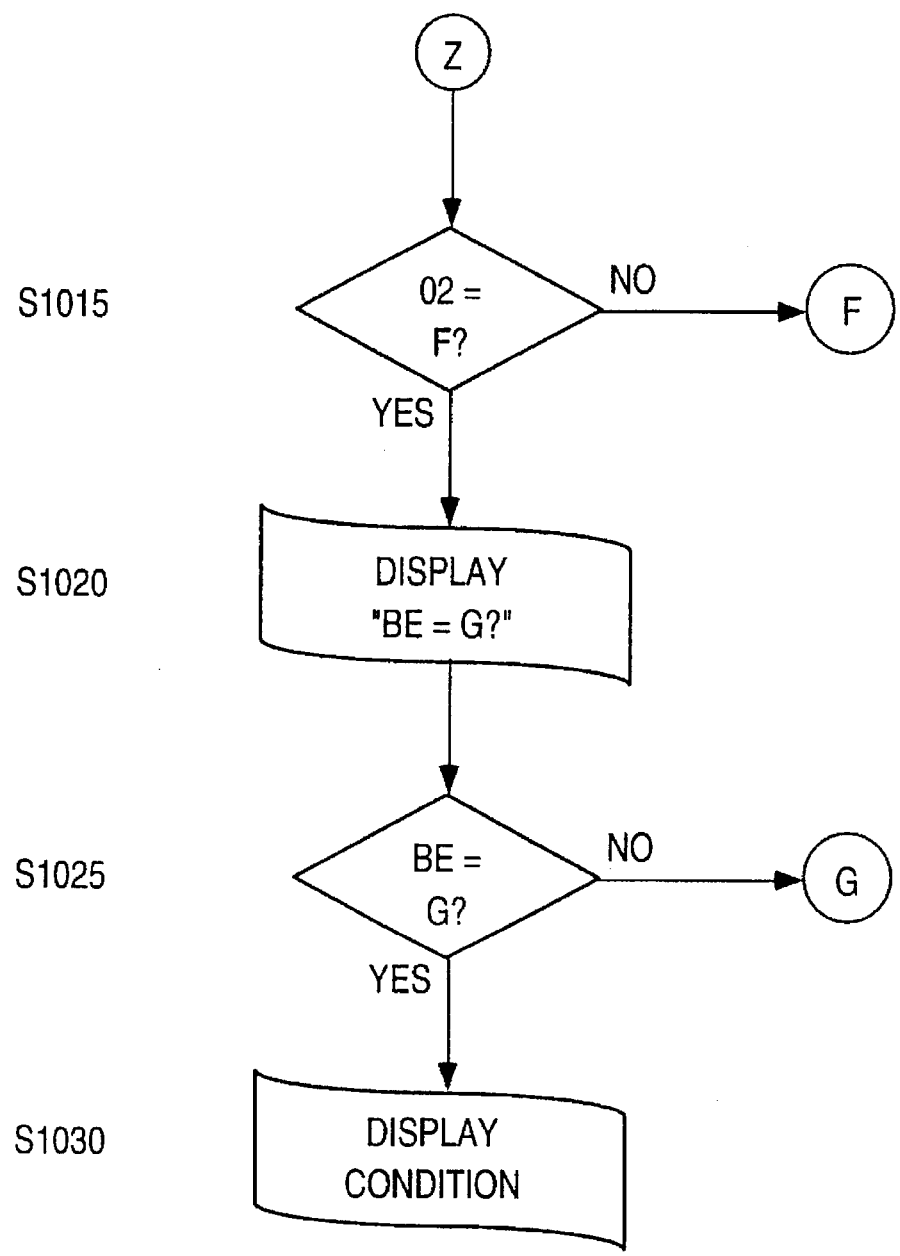

For purpose of illustration, FIG. 14 shows an example of a representative nomogram stored in the memory of the controller 70 of the present invention. This nomogram is related to the interpretation of arterial blood gases and is well known in the medical field. Specifically, the nomogram of FIG. 14 identifies the relationship between various arterial blood gas measurements obtained from a patient and the corresponding condition of the patient. The various measurements entered as data for interpretation include pH, $PaO_2$, $PaCO_2$, $HCO_3$, $H_2CO_3$, $SaO_2$ and BE. Additionally, the age of the patient may be entered, particularly if the patient is over 60 years old. By entering these measurements and using the known relationships of the nomogram of FIG. 14, the following conditions of the patient can be identified: metabolic or respiratory, alkalosis or acidosis, and compensated or uncompensated, as well as normal or mixed imbalance.

The logic flow process used for performing the medical calculation using the stored relationships of FIG. 14 is shown in FIGS. 15A–15D. This logic flow process is selected using the [ABG] key on the data entry pad 20 as shown at step S800. After retrieving the corresponding medical calculation from the memory, the prompt "AGE IN YEARS?" is displayed on the display 50 in accordance with a display signal generated by the controller 70 as shown by step S810. The appropriate age in years is entered using the data entry pad 20 and registered by the [ENTER] key, as shown by step S820. If the age of the patient is not known, the [OVRD] key may be used without entering a value. Subsequent prompts for data provided by the controller 70 include "PH?", "PAO2?", "PCO2?", "HCO3?", "O2?" and "BE?", as shown in steps S830–S940. Once entered, the selected medical calculation is executed by the controller 70 as shown in step S950 of FIGS. 15A–15D by interpreting the entered data relative to the stored relationships to determine the corresponding condition of the patient. Prior to displaying the determined condition, however, each data entry made using the data entry pad 20 must be validated by responding to requests for validation, as shown in steps S960–S1025. If any data entries are incorrect, the controller 70 returns to the appropriate request for data entry.

Once all data entries are validated, the condition determined using the stored relationships of the nomogram is displayed. In this example, the possible conditions displayed include "WNL", "RESP ACIDOSIS COMP", "RESP ALKALOSIS COMP", "MET ACIDOSIS COMP", "MET ALKALOSIS COMP", "RESP ACIDOSIS UNC", "RESP ALKALOSIS UNC", "MET ACIDOSIS UNC", "MET ALKALOSIS UNC", or "MIXED IMBALANCE"; wherein it is understood that "WNL" is an abbreviation for "Within Normal Limits", "RESP" is an abbreviation for "Respiratory", "MET" is an abbreviation for "Metabolic", "COMP" is an abbreviation for "Compensated" and "UNC" is an abbreviation for "Uncompensated". Additionally, the controller 70 is configured to display the percentage of oxygenation that is calculated by reference to the stored relationships of the nomogram based upon the data entered.

MEDICAL CALCULATIONS BASED ON GRAPHICAL INFORMATION

Another medical calculation performed using the hand-held apparatus 100 of the present invention is the calculation of relevant measurements of inputted graphical information. As noted above, graphical information is inputted using the input device and converted into machine readable image data. Therefore, at least one medical calculation is stored within the memory of the controller 70 to calculate a relevant measurement of the inputted graphical information using the machine readable image data.

Generally, the relevant measurement of the inputted graphical information includes an interval having a start point and an end point. The controller 70 embodied herein is configured to calculate the relevant measurement of the inputted graphical information by identifying the start point and the end point and determining the difference therebetween using the image data from the converter 40. A variety of known techniques are available for performing this medical calculation. For example, the start point and end point may be identified by first marking these points on the substrate sheet with a machine readable marker such as a lead pencil and configuring the controller 70 to identify these marked points. Alternatively, the start point and end point may occur naturally at locations of transitions along the graphical information. By digitizing the graphical information into machine readable image data, the controller 70 may be configured to identify the locations of transition corresponding to the relevant start point and end point. Once identified, the coordinates of the start point and end point are determined and the difference therebetween is readily calculated.

In the preferred embodiment of the present invention, the controller 70 is configured to calculate relevant measurements of inputted electrocardiogram (ECG) waveforms. FIG. 16 shows a representative embodiment of an ECG waveform. Transitions occur along the ECG waveform at locations P, Q, R, S, T and U, respectively. As shown in FIG. 16, relevant measurements of the ECG waveform include a PR Interval, a QRS Complex, a QT Segment, and an ST Segment. The controller 70 embodied herein therefore is configured to identify the corresponding locations of transition and determine the difference therebetween to calculate the desired relevant measurement. Similar programs are currently available from Hewlett-Packard Company of Palo Alto, Calif. and Marquette Corometrics, Inc., of Milwaukee, Wis. for multi-lead cardiac machines. Additionally, a ventricular rate of beats per minute may be calculated by determining the distance between two R waves from an inputted electrocardiogram waveform and dividing that distance into the distance corresponding to a 60 second interval. To determine whether the beats are regular of irregular, three R waves must be measured. That is, the distance between the first and second R waves is determined and compared with the distance between the second and third R wave. Using these calculated numerical values corresponding to the selected relevant measurements of the inputted graphical information, a qualified physician can than render a diagnostic interpretation.

In operation, relevant measurements of an ECG waveform from a substrate sheet are calculated by the hand-held apparatus 100 embodied herein in the following manner. The ECG waveform is first printed on an ECG strip using a conventional bedside cardiac monitor or electrocardiograph machine. The controller 70 is initiated by pressing the [ECG] key on the data entry pad 20. After properly aligning the ECG strip with the scanner window 31 using the guides 35,36 as shown in FIG. 7, the scanner 30 is activated using the actuation switch 23. The graphical information from the ECG strip is inputted by moving the ECG across the scanner window 31, either manually by hand or automatically by driven rollers 32. As noted above, this graphical information is converted into machine readable image data signals by the analog-to-digital converter 40 and transmitted to the controller 70. When input is complete, the actuation switch 23 is released. By using medical calculations stored in the memory, the controller 70 may be configured to automatically calculate one or more of the relevant measurements of the inputted graphical information and display the calculated results on the display 50 by generating corresponding display signals, such as "PR=X". Alternatively, the controller 70 may be configured to calculate a relevant measurement of the inputted graphical information in response to the selection of the corresponding medical calculation stored in the memory. For example, the PR Interval of the inputted ECG waveform would be calculated and displayed upon selection of the corresponding medical calculation using the [PR] key on the data entry pad 20.

Using the apparatus of the subject invention, the responsibilities of the nurse or health care professional can be performed more accurately and more uniformly. That is, safe guards are provided to ensure that medical calculations are correct and that data entries are validated. Additionally, the need to rely on personal memory and eyesight to perform calculations and measure ECG waveforms is eliminated. If desired, storage is available to record all calculations and measurements in case review is required.

Although reference has been made to the operation and features of the representative embodiment of the hand-held apparatus of the present invention for the purpose of explanation, it is understood that alternative operations and features likewise may be provided. It also will be apparent to those skilled in the art that various modifications and variations can be made in the design and construction of the hand-held apparatus without departing from the scope or spirit of the invention.

Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

What is claimed is:

1. A hand-held apparatus for performing medical calculations, the apparatus comprising:

a compact housing capable of being held within a hand of an operator;

a data entry pad provided in the housing for selecting one of the medical calculations and entering data required for execution of the selected medical calculation;

a controller provided in the housing in communication with the data entry pad, the controller including a memory having the medical calculations stored therein, the controller being configured to retrieve the selected medical calculation from the memory and provide a prompt for entry of each required data to execute the selected medical calculation, the controller further being configured to provide a request for validation of each data entry made using the data entry pad and to identify a data entry that is outside an expected range corresponding to the prompt for required data, the controller providing a request for re-entry of the identified data entry that is outside the expected range; and a display provided in the housing in communication with the controller, the display being configured to display each prompt for required data and each request for validation, the display further being configured to display the data entry made using the data entry pad, the request for re-entry of the identified data entry and results obtained by execution of the selected medical calculation.

2. The hand-held apparatus of claim 1, wherein at least one of the medical calculations stored in the memory of the controller comprises a determination a medication dose.

3. The hand-held apparatus of claim 1, wherein at least one of the medical calculations stored in the memory of the controller comprises a determination a physical condition of a patient.

4. The hand-held apparatus of claim 1 further comprising a power supply provided in the housing in communication with the controller and an indicator provided in the housing in communication with the power supply, the indicator indicating when power available from the power supply is below a predetermined level.

5. The hand-held apparatus of claim 1 further comprising a chronometer provided on the housing in communication with the controller to provide a desired time measurement.

6. The hand-held apparatus of claim 1 further comprising a second memory provided in the housing, the second memory being configured to store the results of the selected medical calculations executed by the controller.

7. The hand-held apparatus of claim 1 further comprising a scanner and a converter provided in the housing in communication with the controller, the scanner being configured to input graphical information, the converter being in communication with the scanner and configured to convert the graphical information into corresponding machine readable image data recognized by the controller, at least one of the medical calculations stored within the memory being capable of calculating a relevant measurement of the graphical information using the image data from the converter.

8. The hand-held apparatus of claim 7, wherein the scanner is configured to input electrocardiogram waveform graphical information, the relevant measurement of the electrocardiogram waveform graphical data including at least one of a PR Interval, a QRS Complex, a QT Segment, an ST Segment, and a ventricular rate of beats per minute.

9. A hand-held apparatus for performing medical calculations, the apparatus comprising:

a compact housing capable of being held within a hand of an operator;

a data entry pad provided in the housing for selecting one of the medical calculations and entering data required for execution of the selected medical calculation;

a memory provided in the housing, the memory having the medical calculations stored therein;

means provided in the housing and in communication with the memory for retrieving the selected medical calculation;

means provided in the housing for executing the selected medical calculation, the executing means providing a prompt for entry of the required data using the data entry pad;

means provided within the housing for validating the data entry made using the data entry pad, the validating means providing a request for validation;

means provided in the housing for inputting graphical information, at least one of the medical calculations stored in the memory and executed by the executing means being capable of calculating a relevant measurement of the inputted graphical information; and a display provided in the housing in communication with the executing means and the validating means, the display being configured to display each prompt for required data and each request for validation, the display further being configured to display the data entry made using the data entry pad and results obtained by execution of the selected medical calculation.

10. The hand-held apparatus of claim 9 further comprising a second memory provided in the housing, the second memory being configured to store the results of the selected medical calculations executed by the executing means.

11. The hand-held apparatus of claim 9, wherein the executing means and the validating means include a controller configured to execute the selected medical calculation and to validate the data entry made using the data entry pad.

12. The hand-held apparatus of claim 9, wherein the inputting means is configured to input electrocardiogram waveform graphical information, the relevant measurement from the electrocardiogram waveform graphical information including at least one of a PR Interval, a QRS Complex, an ST Segment and a ventricular rate of beats per minute.

13. The hand-held apparatus of claim 9, wherein the inputting means is a scanner configured to input the graphical information and the calculating means is a controller having a memory with at least one medical calculation stored therein for calculating the relevant measurement of the inputted graphical information, the apparatus further comprising a converter configured to convert the graphical information from the scanner into corresponding machine readable image data recognized by the controller, the controller being configured to retrieve the medical calculation from the memory and execute the medical calculation using the image data from the converter.

14. A hand-held apparatus for performing medical calculations, the apparatus comprising:

a compact housing capable of being held within a hand of an operator;

a scanner provided in the housing, the scanner being configured to input graphical information;

a converter provided in the housing in communication with the scanner, the converter being configured to convert the graphical information into corresponding machine readable image data;

a controller provided in the housing in communication with the converter, the controller being configured to calculate a relevant measurement of the graphical information using the image data from the converter; and a display provided in the housing in communication with the controller, the display being configured to display the relevant measurement calculated by the controller.

15. The hand-held apparatus of claim 14, wherein the relevant measurement of the inputted graphical information includes an interval having a start point and an end point, the controller being configured to calculate the relevant measurement of the inputted graphical information by identifying the start point and the end point and determining the difference therebetween using the image data from the converter.

16. The hand-held apparatus of claim 14, wherein the scanner is configured to input electrocardiogram waveform graphical information, the relevant measurement from the electrocardiogram waveform graphical data including at least one of a PR Interval, a QRS Complex, a QT Segment, an ST Segment and a ventricular rate of beats per minute.

17. The hand-held apparatus of claim 14, wherein the scanner includes a scanner window and is configured to input graphical information from a substrate sheet, the apparatus further comprising a guide located proximate the scanner to ensure proper alignment of the substrate sheet relative to the scanner window.

18. The hand-held apparatus of claim 14, wherein the scanner includes a scanner window and is configured to input graphical information from a substrate sheet, the apparatus further comprising a roller to feed the substrate sheet across the scanner window at a predetermined speed.

19. The hand-held apparatus of claim 14, wherein the scanner includes a scanner window, the apparatus further comprising a cover moveable between a closed position to protect the scanner window and an open position to expose the scanner window.

20. The hand-held apparatus of claim 14, wherein the controller includes a memory having at least one medical calculation stored therein for calculating the relevant measurement of the inputted graphical information using the image data from the converter, the controller being configured to retrieve the medical calculation from the memory and execute the medical calculation using the image data from the converter.

21. The hand-held apparatus of claim 20, wherein the memory of the controller further includes medical calculations related to treatment of a patient stored therein, the apparatus further comprising a data entry pad provided in the housing in communication with the controller for selecting one of the medical calculations and entering data required for execution of the selected medical calculation, the display further being configured to display the data entry made using the data entry pad and results obtained by execution of the selected medical calculation.

22. The hand-held apparatus of claim 21, wherein the controller includes means to provide a prompt for entry of each required data and a request for validation of each data entry made using the data entry pad, the display being in communication with the controller to display the prompt for data and the request for validation provided by the controller.

23. A hand-held apparatus for performing medical calculations, the apparatus comprising:

a compact housing capable of being held within a hand of an operator;

means provided in the housing for inputting graphical information;

means provided in the housing and in communication with the inputting means for calculating a relevant measurement of the inputted graphical information; and a display provided in the housing in communication with the calculating means for displaying the relevant measurement of the inputted graphical information calculated by the calculating means.

24. The hand-held apparatus of claim 23, wherein the relevant measurement of the inputted graphical information includes an interval having a start point and an end point, the calculating means identifying the start point and the end point and determining the difference therebetween.

25. The hand-held apparatus of claim 23, wherein the inputting means is configured to input electrocardiogram waveform graphical information, the relevant measurement from the electrocardiogram waveform graphical data including at least one of a PR Interval, a QRS Complex, a QT Segment, an ST Segment and a ventricular rate of beats per minute.

26. The hand-held apparatus of claim 23, wherein the inputting means is a scanner configured to input the graphical information and the calculating means is a controller having a memory with at least one medical calculation stored therein for calculating the relevant measurement of the inputted graphical information, the apparatus further comprising a converter configured to convert the graphical information from the scanner into corresponding machine readable image data recognized by the controller, the controller being configured to retrieve the medical calculation from the memory and execute the medical calculation using the image data from the converter.

* * * * *